(12) United States Patent
Potyrailo et al.

(10) Patent No.: US 7,911,345 B2
(45) Date of Patent: Mar. 22, 2011

(54) METHODS AND SYSTEMS FOR CALIBRATION OF RFID SENSORS

(75) Inventors: Radislav Alexandrovich Potyrailo, Niskayuna, NY (US); William Guy Morris, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 513 days.

(21) Appl. No.: 12/118,950

(22) Filed: May 12, 2008

(65) Prior Publication Data

US 2009/0278685 A1 Nov. 12, 2009

(51) Int. Cl.
*G08B 13/00* (2006.01)

(52) U.S. Cl. .................... 340/572.1; 340/10.1; 340/10.5

(58) Field of Classification Search ............... 340/572.1, 340/10.1, 10.5
See application file for complete search history.

(56) References Cited

U.S. PATENT DOCUMENTS

| | | | |
|---|---|---|---|
| 7,089,099 B2 | 8/2006 | Shostak et al. | |
| 7,109,859 B2 | 9/2006 | Peeters | |
| 7,148,803 B2 | 12/2006 | Bandy et al. | |
| 7,439,860 B2 * | 10/2008 | Andresky | 340/572.1 |
| 2003/0042149 A1 | 3/2003 | Smith et al. | |
| 2005/0087235 A1 | 4/2005 | Skorpik et al. | |
| 2005/0088299 A1 | 4/2005 | Bandy et al. | |
| 2005/0104790 A1* | 5/2005 | Duron | 343/745 |
| 2005/0130292 A1 | 6/2005 | Ahn et al. | |
| 2006/0131697 A1 | 6/2006 | Wu et al. | |
| 2006/0202821 A1 | 9/2006 | Cohen | |
| 2006/0290496 A1 | 12/2006 | Peeters | |
| 2007/0072009 A1 | 3/2007 | Matsumoto et al. | |
| 2007/0090927 A1 | 4/2007 | Potyrailo et al. | |

(Continued)

FOREIGN PATENT DOCUMENTS

WO WO02095675 11/2002

(Continued)

OTHER PUBLICATIONS

PCT International Search Report dated Jul. 10, 2009.

(Continued)

*Primary Examiner* — Travis R Hunnings
(74) *Attorney, Agent, or Firm* — Eileen W. Gallagher

(57) ABSTRACT

Methods and systems for calibration of RFID sensors used in manufacturing and monitoring systems are provided. The methods include measuring impedance of an RFID sensor antenna, relating the measurement of impedance to one or more parameters (such as physical, chemical and biological properties), computing one or more analytical fit coefficients, and storing the one or more analytical fit coefficients on a memory chip of the RFID sensor. Measuring impedance of the RFID sensor may comprise measuring complex impedance which involves measuring complex impedance spectrum, phase angle and magnitude of the impedance, at least one of frequency of the maximum of the real part of the complex impedance, magnitude of the real part of the complex impedance, zero-reactance frequency, resonant frequency of the imaginary part of the complex impedance, and antiresonant frequency of the imaginary part of the complex impedance. Also provided are manufacturing or monitoring systems comprised of an RFID sensor wherein the RFID sensor comprises, a memory chip, an antenna, and a sensing film wherein analytical fit coefficients are stored on the memory chip to allow calibration of the RFID sensor. Also provided are manufacturing or monitoring systems comprised of an RFID sensor wherein the RFID sensor comprises, a memory chip, an antenna, and a complementary sensor attached to the antenna where the complementary sensor in a pre-calibrated fashion predictably affects the impedance of the antenna.

29 Claims, 25 Drawing Sheets

U.S. PATENT DOCUMENTS

| | | | |
|---|---|---|---|
| 2007/0100666 A1 | 5/2007 | Stivoric et al. | |
| 2007/0213684 A1 | 9/2007 | Hickle et al. | |
| 2007/0215709 A1 | 9/2007 | Baude et al. | |
| 2007/0222605 A1* | 9/2007 | Andresky | 340/572.7 |
| 2008/0004904 A1 | 1/2008 | Tran | |
| 2008/0012577 A1 | 1/2008 | Potyrailo et al. | |
| 2008/0024301 A1 | 1/2008 | Fritchie et al. | |
| 2008/0033368 A1 | 2/2008 | Fago | |
| 2008/0164977 A1* | 7/2008 | Butler et al. | 340/10.1 |
| 2009/0204250 A1* | 8/2009 | Potyrailo et al. | 700/109 |
| 2009/0289776 A1* | 11/2009 | Moore et al. | 340/10.41 |
| 2010/0134257 A1* | 6/2010 | Puleston et al. | 340/10.4 |
| 2010/0225482 A1* | 9/2010 | Kasai et al. | 340/572.1 |

FOREIGN PATENT DOCUMENTS

| | | |
|---|---|---|
| WO | WO03098175 | 11/2003 |
| WO | WO2006131697 | 12/2006 |
| WO | WO2007072009 | 6/2007 |

OTHER PUBLICATIONS

Dorneanu et al., "Computer-controlled System for ISEs Automatic Calibration", Sensors and Actuators, 105 (2005), 521-531.

Rivera et al., "Self-Calibration and Optimal Response in Intelligent Sensors Design Based on Artificial Neural Networks", Sensors, (2007) 7, 1509-1529.

Setter et al., "Redundant Chemical Sensors for Calibration-Impossible Applications", Talanta 54, (2001), 99-106.

Kim et al., "Manipulation of Microenvironment With a Built-In Electrochemical Actuator in Proximity of a Dissolved Oxygen Microsensor", IEEE Sensors Journal, vol. 4, No. 5, Oct. 2004, 568-575.

Berntsson et al., "Multivariate Experimental Methodology Applied to the Calibration of a Clark Type Oxygen Sensor", Analyitca Chimica Acta 355, (1997) 43-53.

Fabrizio et al., "Dynamic Calibration of QMB Polymer-Coated Sensors by Wiener Kernel Estimation", Sensors and Actuators B, 26-27 (1995) 275-285.

Potyrailo et al., "Multianalyte Chemical Identification and Quantitation Using a Single Radio Frequency Identification Sensor", Analytical Chemistry 2007, 79, No. 1, Jan. 1, 2007, 45-51.

Potyrailo et al., "Position-Independent Chemical Quantitation with Passive 13.56-MHz Radio Frequency Identification (RFID) Sensors", Talanta, Jun. 13, 2007, 624-628.

Colwell, Rita et al., "Creating a Nationwide Wireless Detection Sensor Network for Chemical, Boiological and Radiological Threads", Gentag, Aug. 2007, pp. 1-4.

Oertel, Britta et al., "Security Aspects and Prospective Applications of RFID Systems", Oct. 2004, pp. 1-120 (Parts 1, 2, & 3).

Kanne, U. et al., "Digital Flow Sensors", Medical Device Technology, Jun. 2006, pp. 12-14.

Kirschenbaum, Han et al., "How to Build a Low-Cost, Extended-Range RFID Skimmer", Feb. 2, 2006, pp. 1-22.

Hearst Smiconductor Applications, "Disposable Healthcare Chip Allowing Multi-item Diagnostics in a Trace of Blood", pp. 1-2.

\* cited by examiner

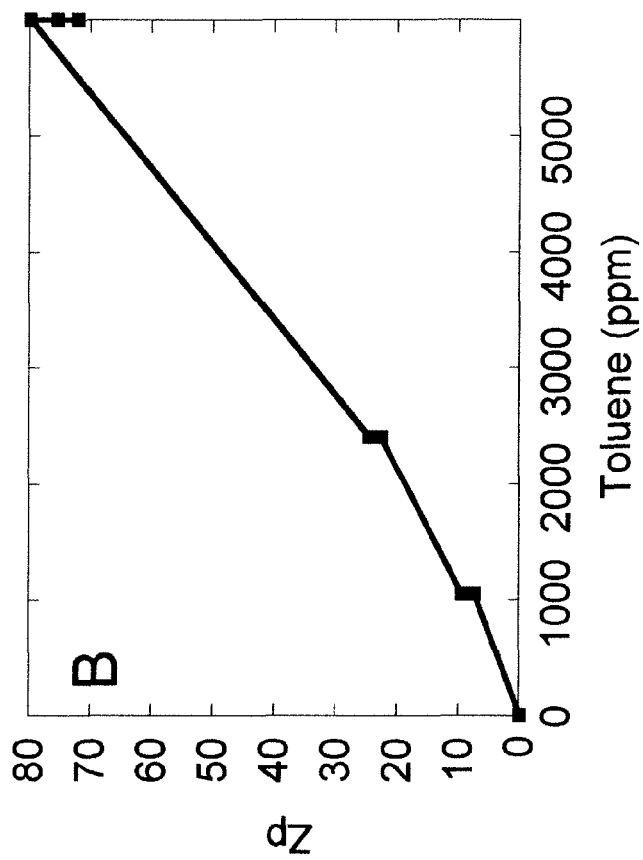
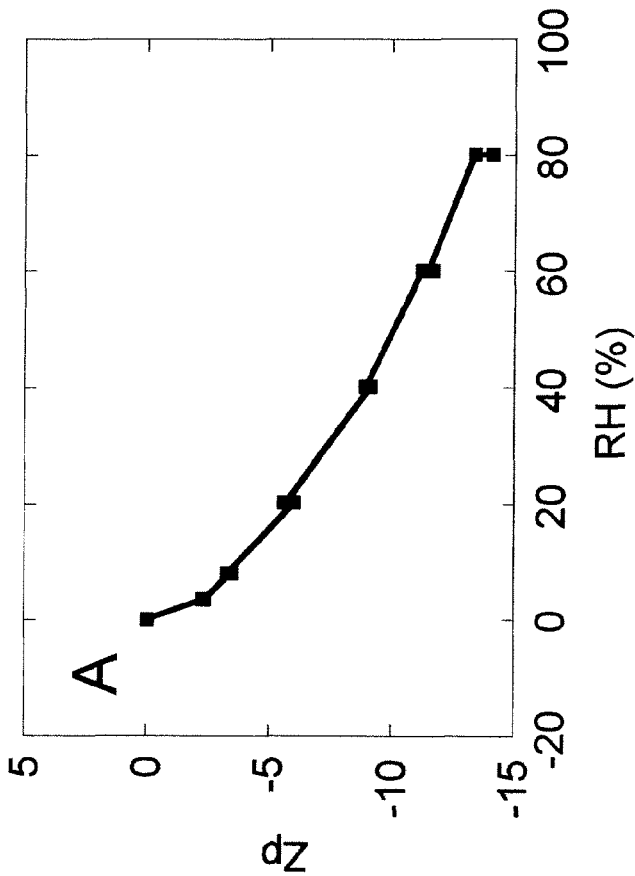
Fig. 18A
Fig. 18b

METHODS AND SYSTEMS FOR CALIBRATION OF RFID SENSORS

BACKGROUND

The invention relates generally to radio frequency identification (RFID) sensors used in manufacturing and monitoring systems comprised of single use or multi-use components, and more particularly to a system and method for calibrating the RFID sensors.

Single use, disposable, equipment and components have gained significant interest from the manufacturing community especially the biopharmaceutical, food, beverage, and packaging industries. Single use, disposable monitoring equipment has gained significant interest also from the monitoring community, especially first responders. Single use components offer flexibility, mobility, overall process efficiency as well as reduction in cleaning and sterilization protocols, lower risk of cross-contamination, and reduced manufacturing capital cost. Full ranges of single use, disposable technologies for biopharmaceutical production are commercially available for simple operations such as buffer storage and mixing and are rapidly expanding into complex application such as fermentation. Monitoring of process parameters may be accomplished using RFID sensors positioned throughout disposable systems.

Accurate monitoring of key environmental parameters using disposable RFID sensors is important to secure safety and process documentation as well as to eliminate the risk of cross contamination between manufacturing operations. In food, beverage, and packaging industries, accurate monitoring of key environmental parameters with RFID sensors is useful in protecting food and beverage quality. However, the acceptance of disposable monitoring technologies is hindered by the absence of RFID sensors having the degree of scientific accuracy required. This lack of accuracy relates in part to the unavailability of calibration methods for the RFID sensors. Thus, there is a need for a technology solution that can provide a calibration method for non-invasive RFID monitoring technology with scientific accuracy. The calibration method has application in both single use and multi-use components.

BRIEF DESCRIPTION

The present invention provides a calibration method for non-invasive RFID monitoring technology with application in both single use and multi-use components.

In some embodiments a method for calibration of an RFID sensor used in manufacturing and monitoring systems is provided and comprises measuring impedance of an RFID sensor antenna, relating the measurement of impedance of the RFID sensor antenna to one or more parameters, computing one or more analytical fit coefficients, and storing the one or more analytical fit coefficients on a memory chip of the RFID sensor.

In accordance with another embodiment measuring impedance of the RFID sensor comprises measuring complex impedance which involves measuring at least one of frequency of the maximum of the real part of the complex impedance, magnitude of the real part of the complex impedance, resonant frequency of the imaginary part of the complex impedance, antiresonant frequency of the imaginary part of the complex impedance, zero-reactance frequency, phase angle, and magnitude of impedance.

In accordance with another embodiment, a manufacturing or monitoring system is provided and comprises an RFID sensor wherein the RFID sensor comprises, a memory chip, an antenna, and a sensing film wherein analytical fit coefficients are stored on the memory chip to allow calibration of the RFID sensor.

In accordance with another embodiment, a manufacturing or monitoring system is provided and comprises an RFID sensor wherein the RFID sensor comprises, a memory chip, an antenna, and a complementary sensor across an antenna and memory chip, where the electrical response of the complementary sensor is translated into changes in the complex impedance response of the antenna, resonance peak position, peak width, peak height, peak symmetry of the complex impedance response of the antenna, magnitude of the real part of the complex impedance, resonant frequency of the imaginary part of the complex impedance, antiresonant frequency of the imaginary part of the complex impedance, zero-reactance frequency, phase angle, and magnitude of impedance.

In accordance with yet another embodiment a method of operating a calibrated RFID sensor is provided and comprises measuring impedance of an RFID sensor during exposure to one or more parameters, converting the impedance into measurement values of the one or more parameters using the stored one or more analytical fit coefficients, storing measurement values in memory of the memory chip of the RFID sensor by writing the measurement values using a reader/writer device, and optionally sending the measurement values of the one or more parameters to a display device or a control.

DRAWINGS

These and other features, aspects, and advantages of the present invention will become better understood when the following detailed description is read with reference to the accompanying drawings.

Figure 13:
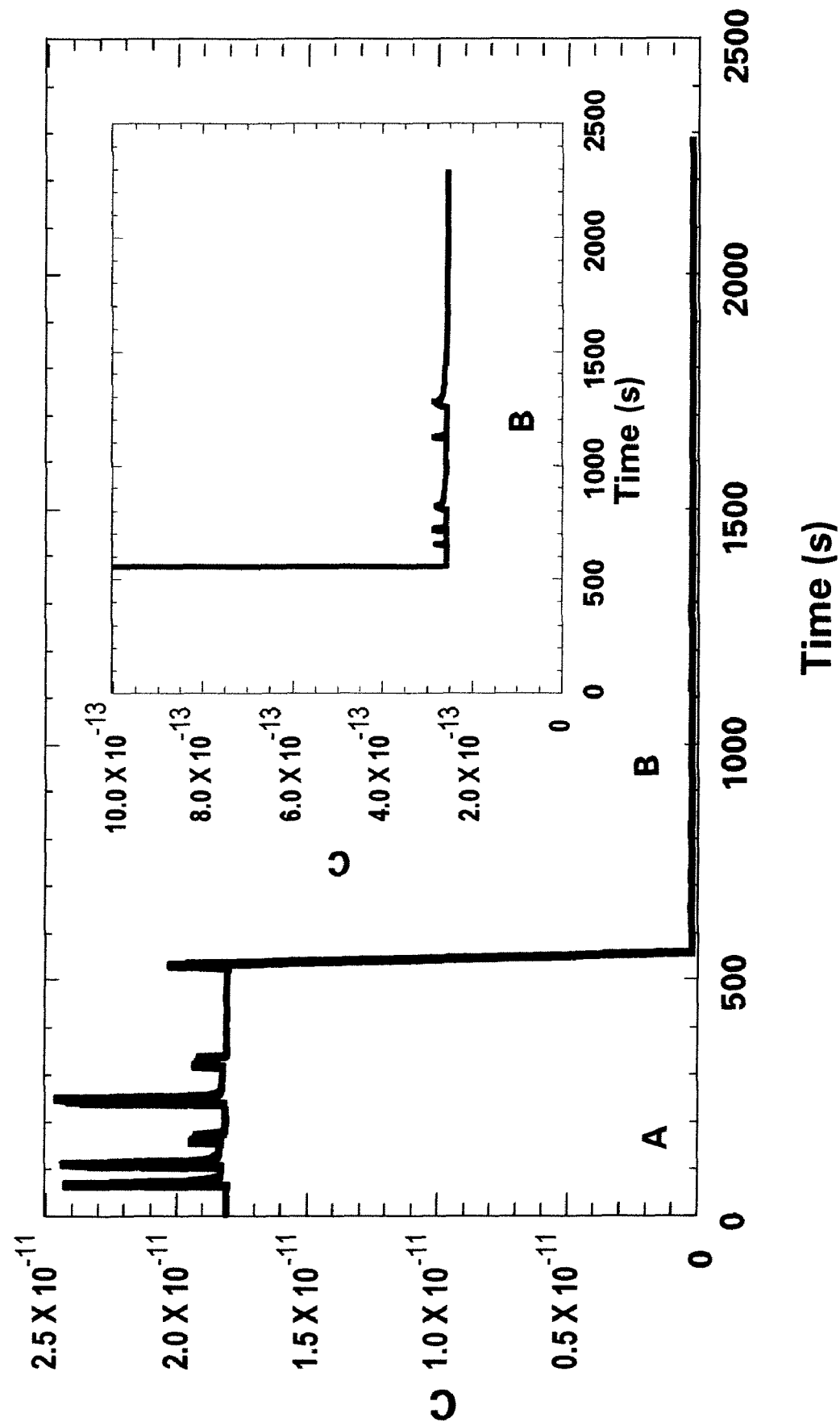
Figure 14B:
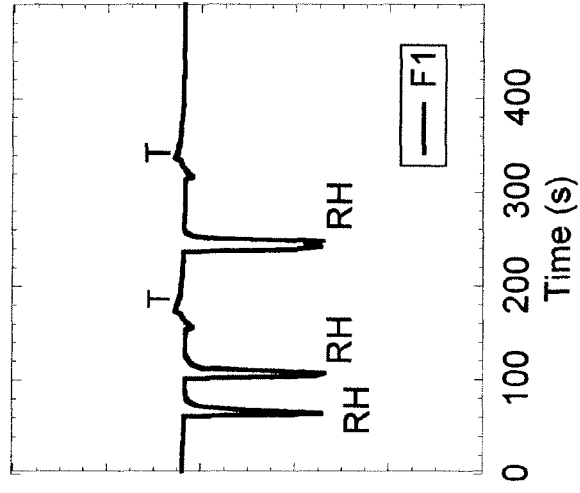
Figure 14D:
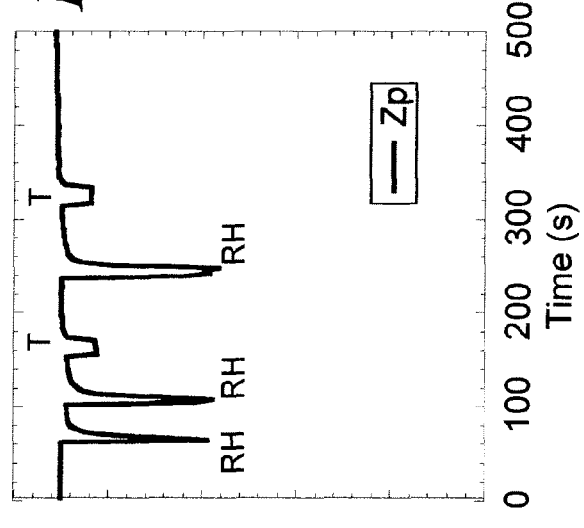
Figure 14A:
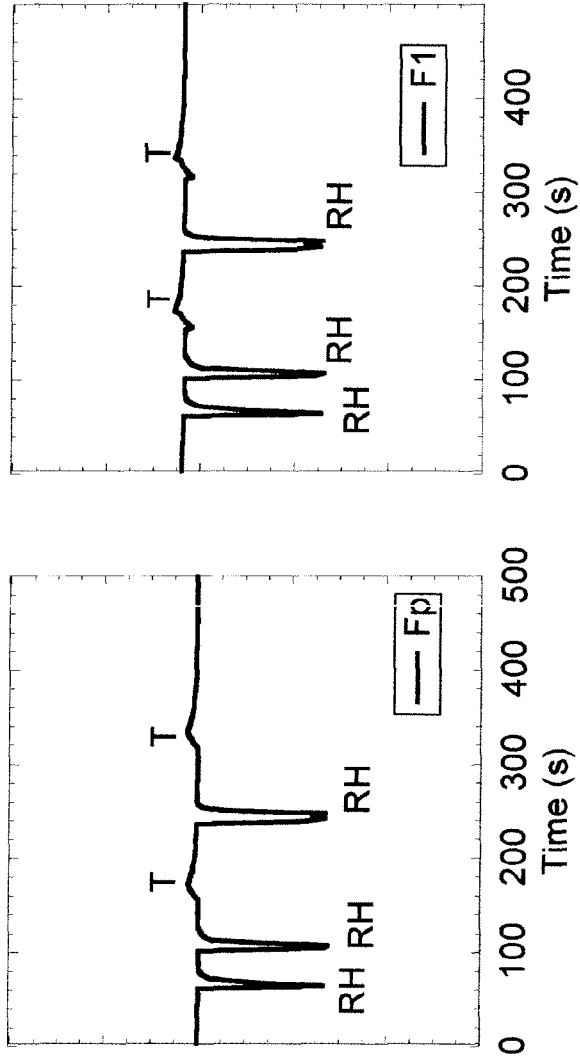
Figure 14C:
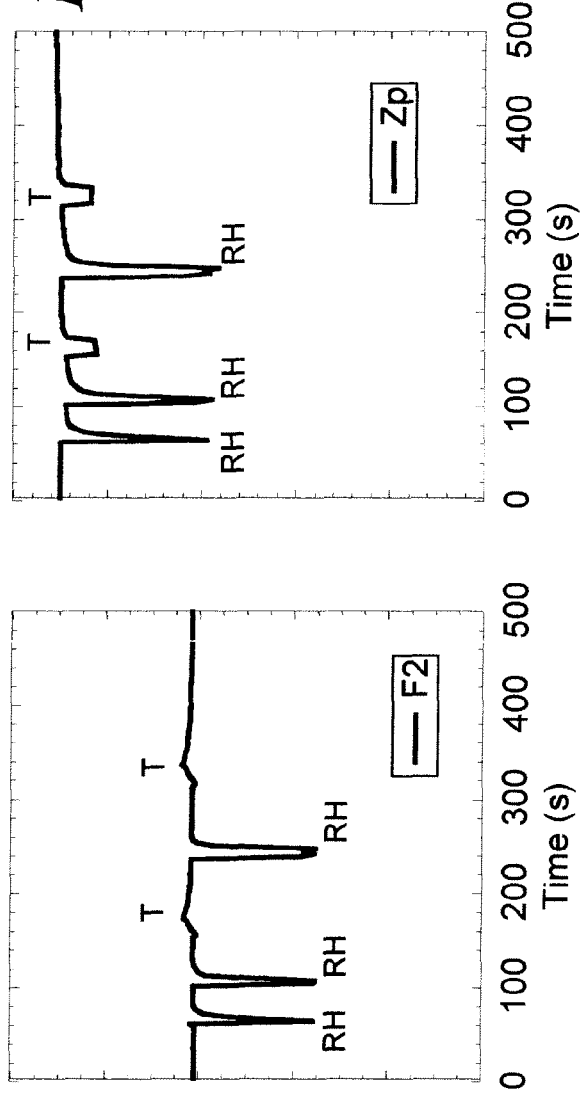
Figure 15B:
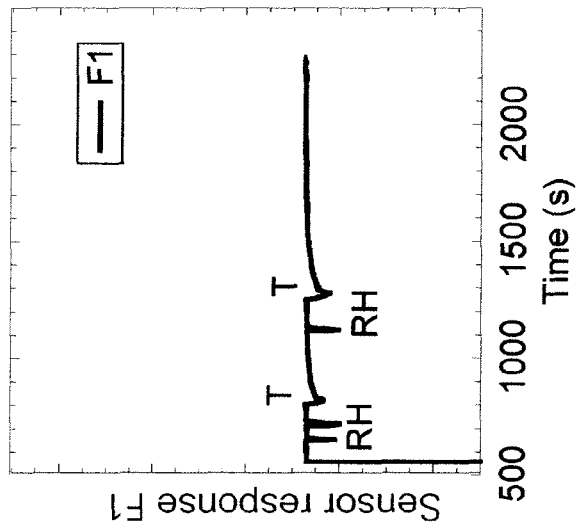
Figure 15D:
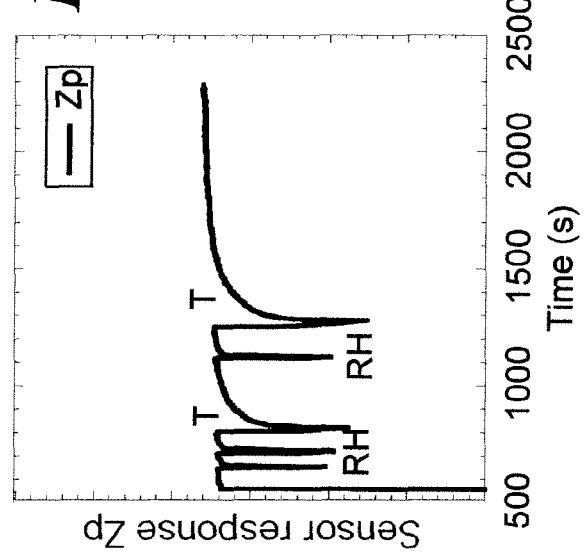
Figure 15A:
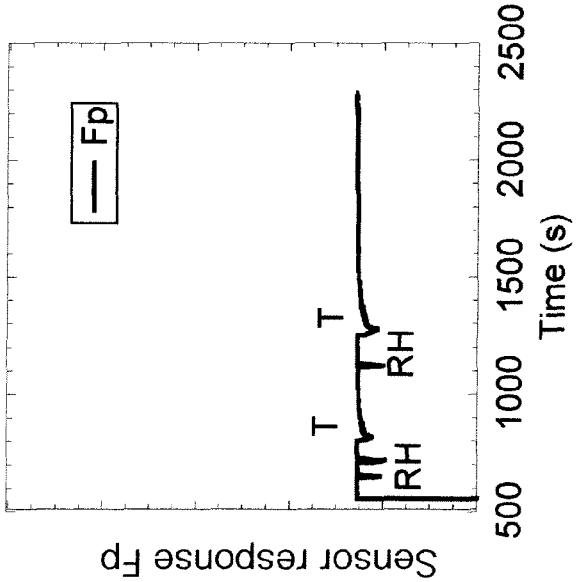
Figure 15C:
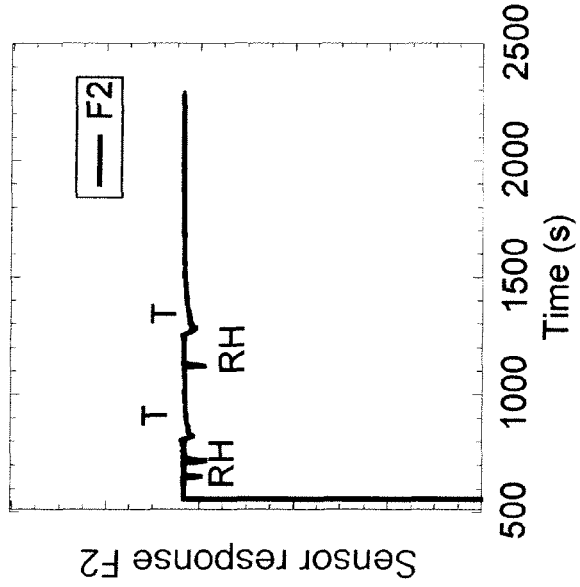

FIG. 13 compares the measured responses of an embodiment of an RFID sensor resulting from humidity changes, with and without an attached complementary capacitance sensor.

FIG. 14 illustrates the ability of an embodiment of an RFID sensor to discriminate between temperature and humidity effects using Fp, F1, F2, and Zp response parameters.

FIG. 15 shows the measured response of an embodiment of an RFID sensor resulting from humidity and temperature changes.

Figure 16:
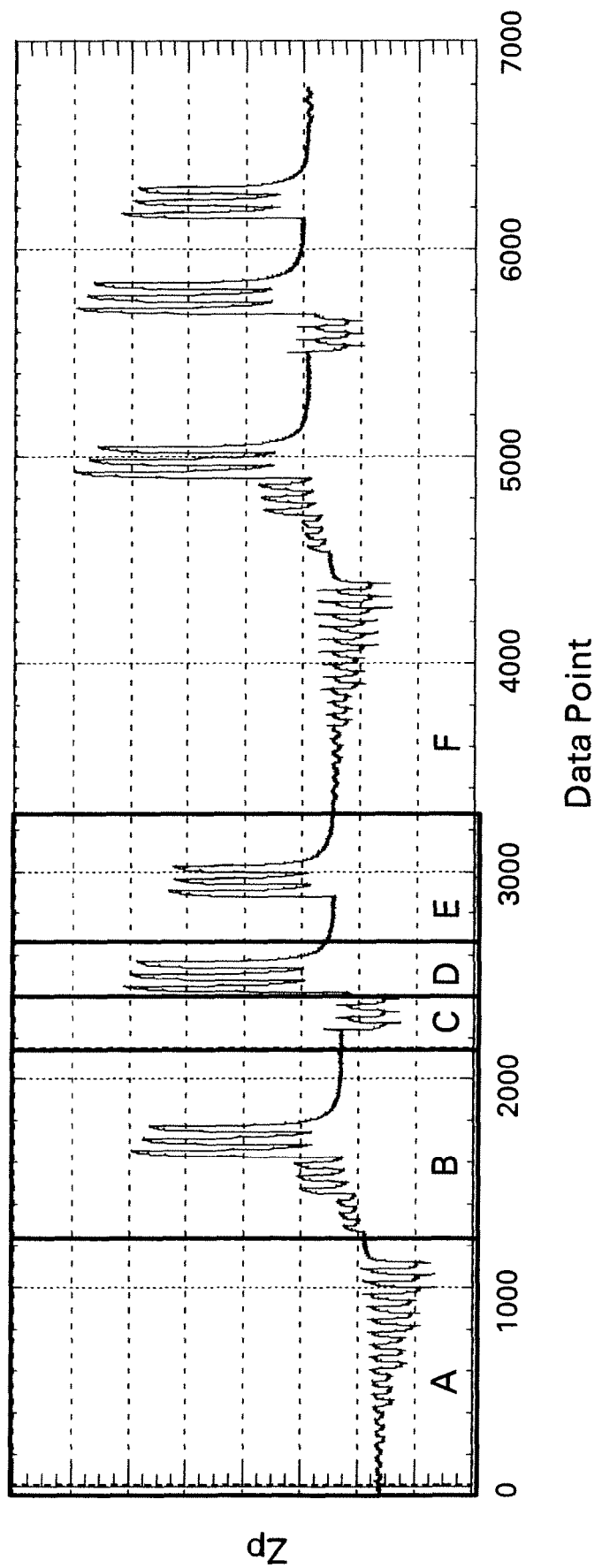

FIG. 16 shows the measured complex response of an embodiment of an RFID sensor resulting from exposure to water and toluene vapors and their mixtures.

FIG. 17 shows the regions the measured complex response of an embodiment of an RFID sensor resulting from exposure to different concentrations of (A) water vapor and (B) toluene vapor.

FIG. 18 shows calibration plots of the measured response of an embodiment of an RFID sensor for two different vapors: (A) water vapor as relative humidity and (B) toluene vapor.

Figure 19B:
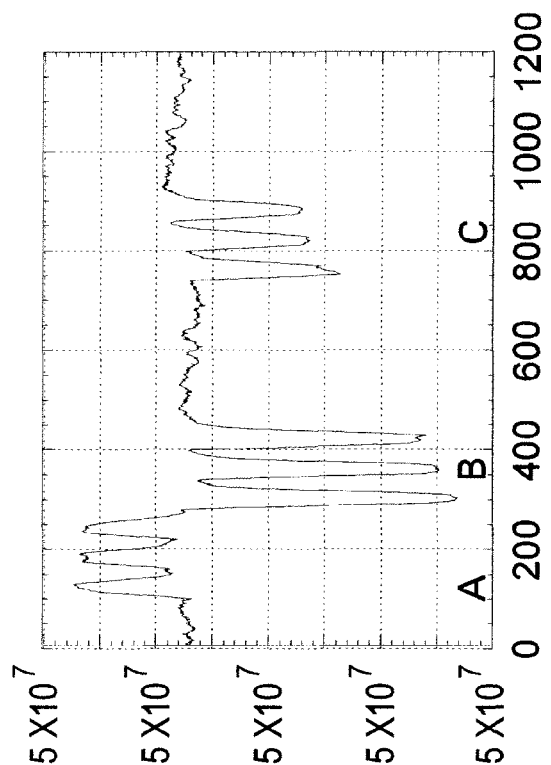
Figure 19A:
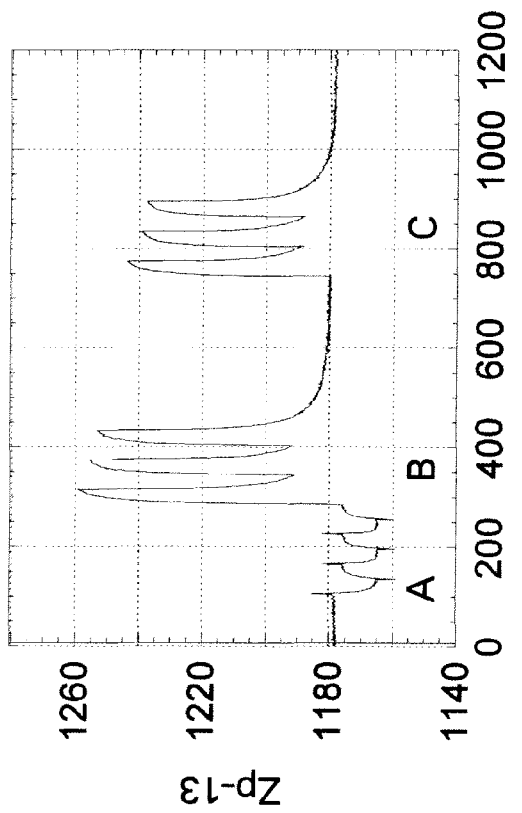

FIG. 19 shows the measured response of an embodiment of an RFID sensor response to individual components and to mixtures of water vapor and toluene vapor.

Figure 20:
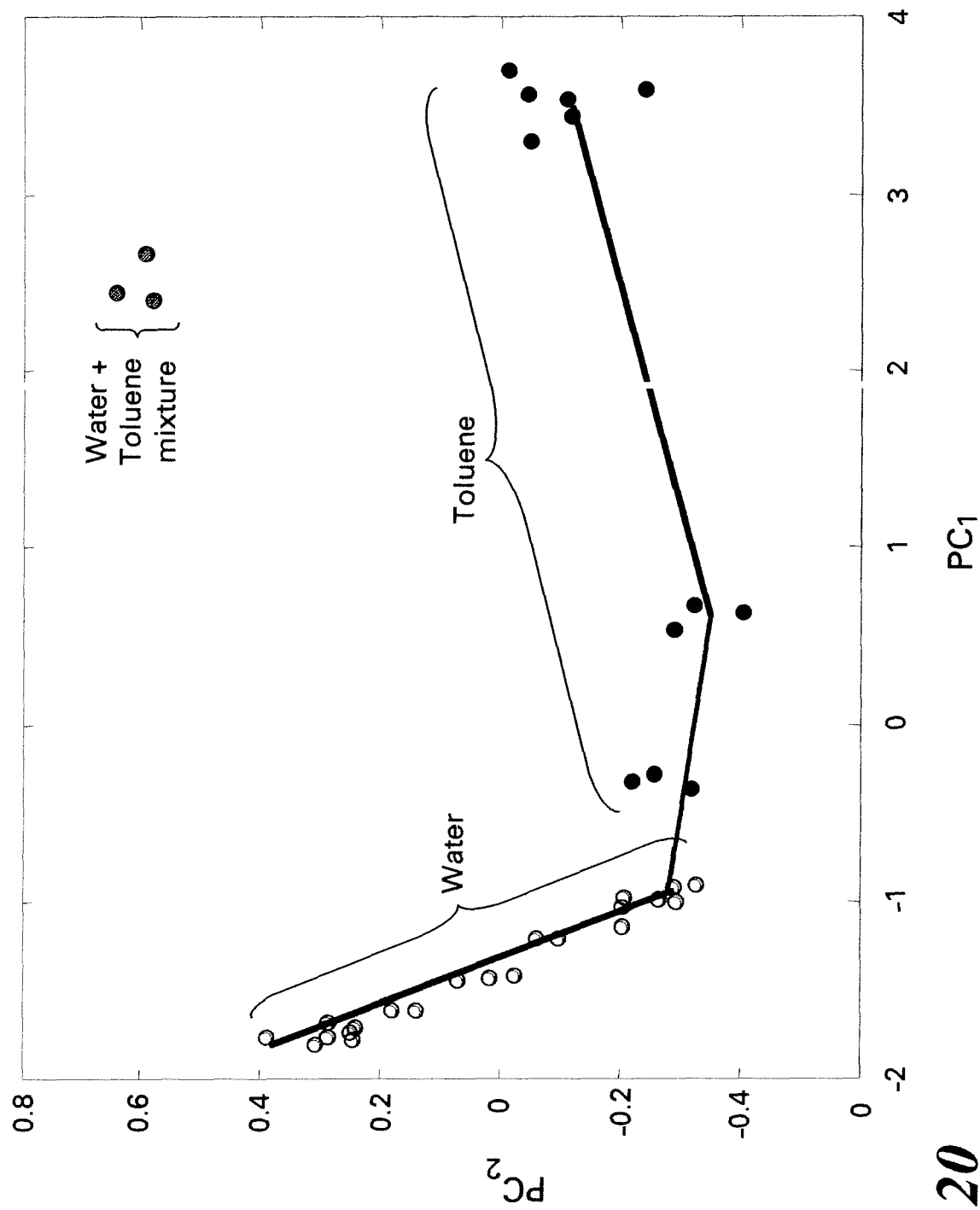
Figure 21B:
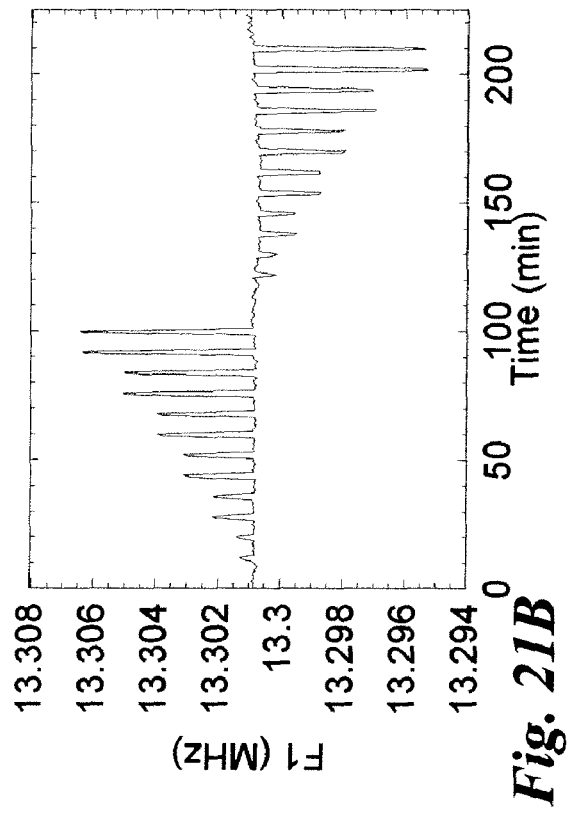
Figure 21D:
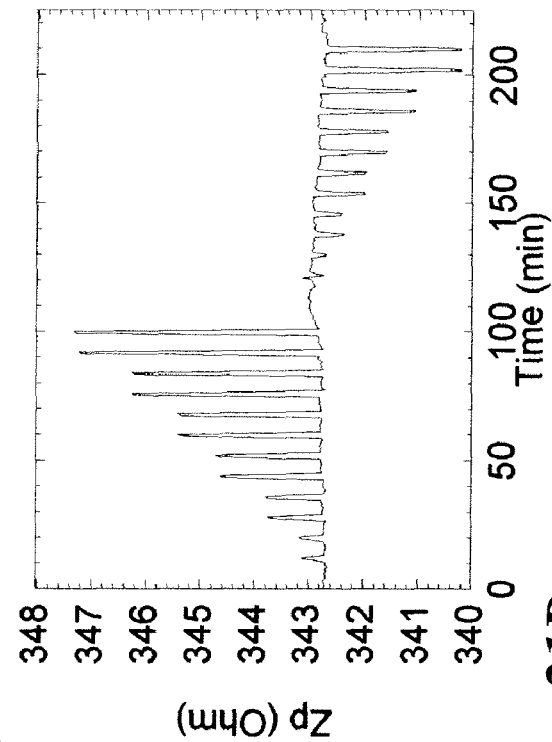
Figure 21A:
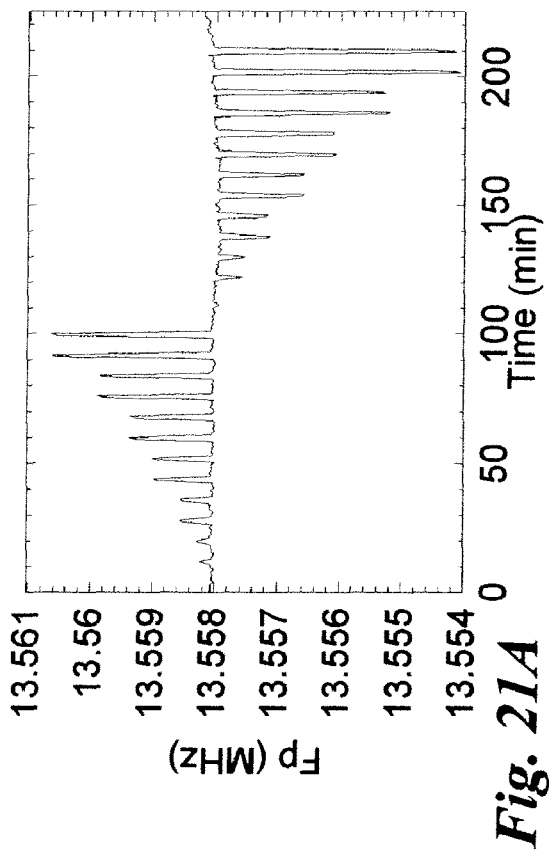
Figure 21C:
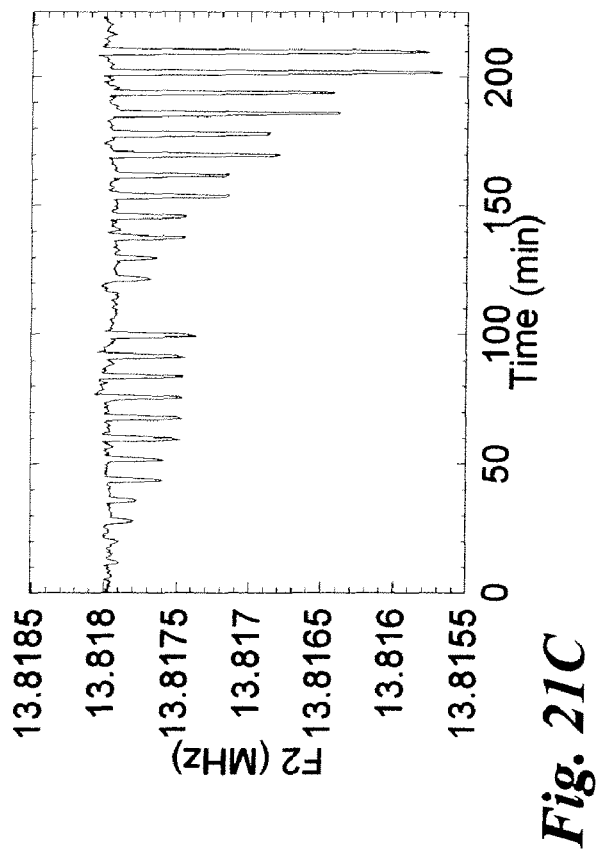

FIG. 20 shows the results of principal components analysis, which demonstrates that an embodiment of an RFID sensor was able to resolve a mixture of toluene and water vapors.

FIG. 21 shows a response pattern of an embodiment of an RFID sensor having an attached capacitance vapor sensor.

Figure 22:
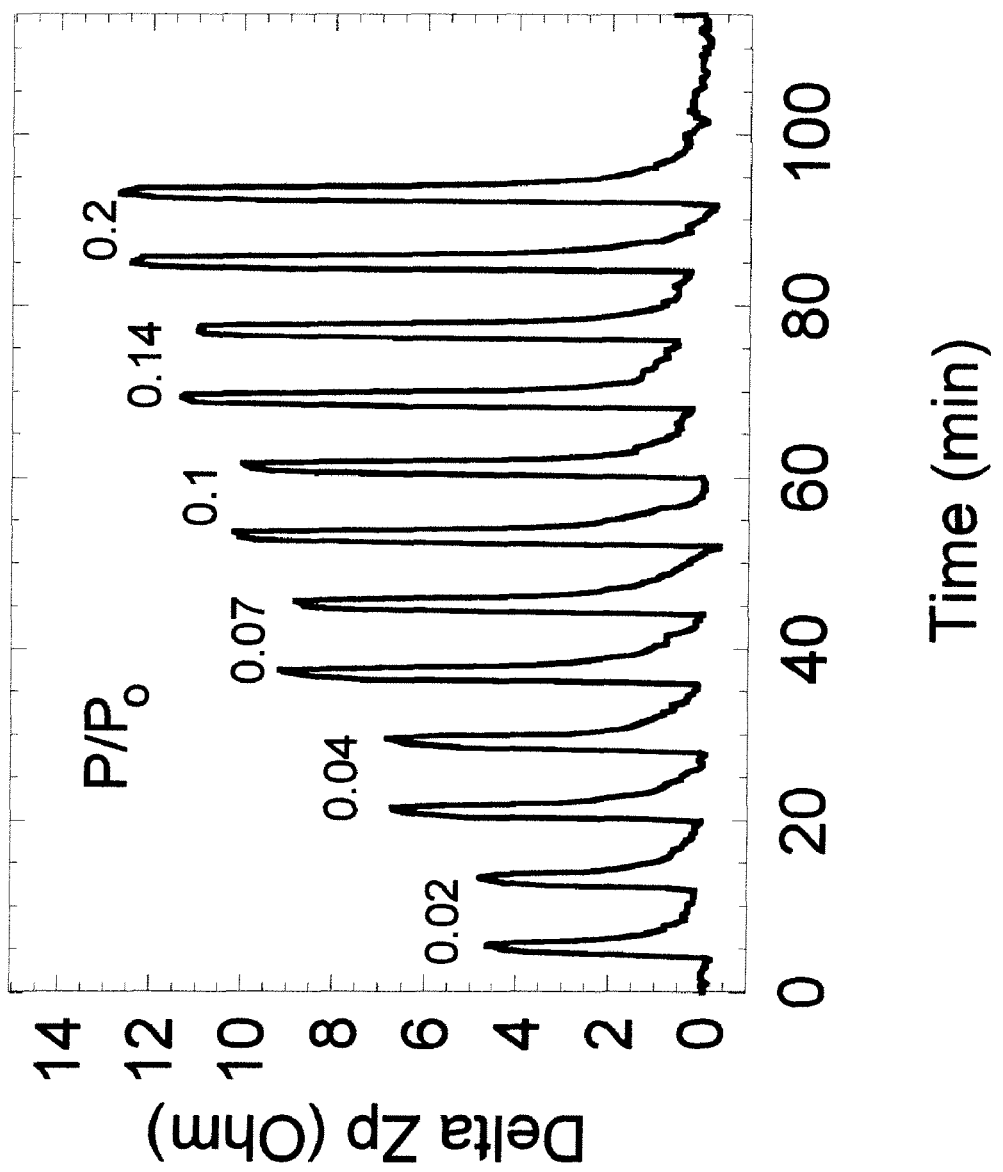

FIG. 22 shows the operation of an embodiment of a resistive RFID complementary sensor used for monitoring dichloromethane vapor; the RFID sensor was exposed to six vapor concentrations (0.02, 0.04, 0.7, 0.1, 0.14, and 0.2 P/Po) with two replicates.

Figure 23:
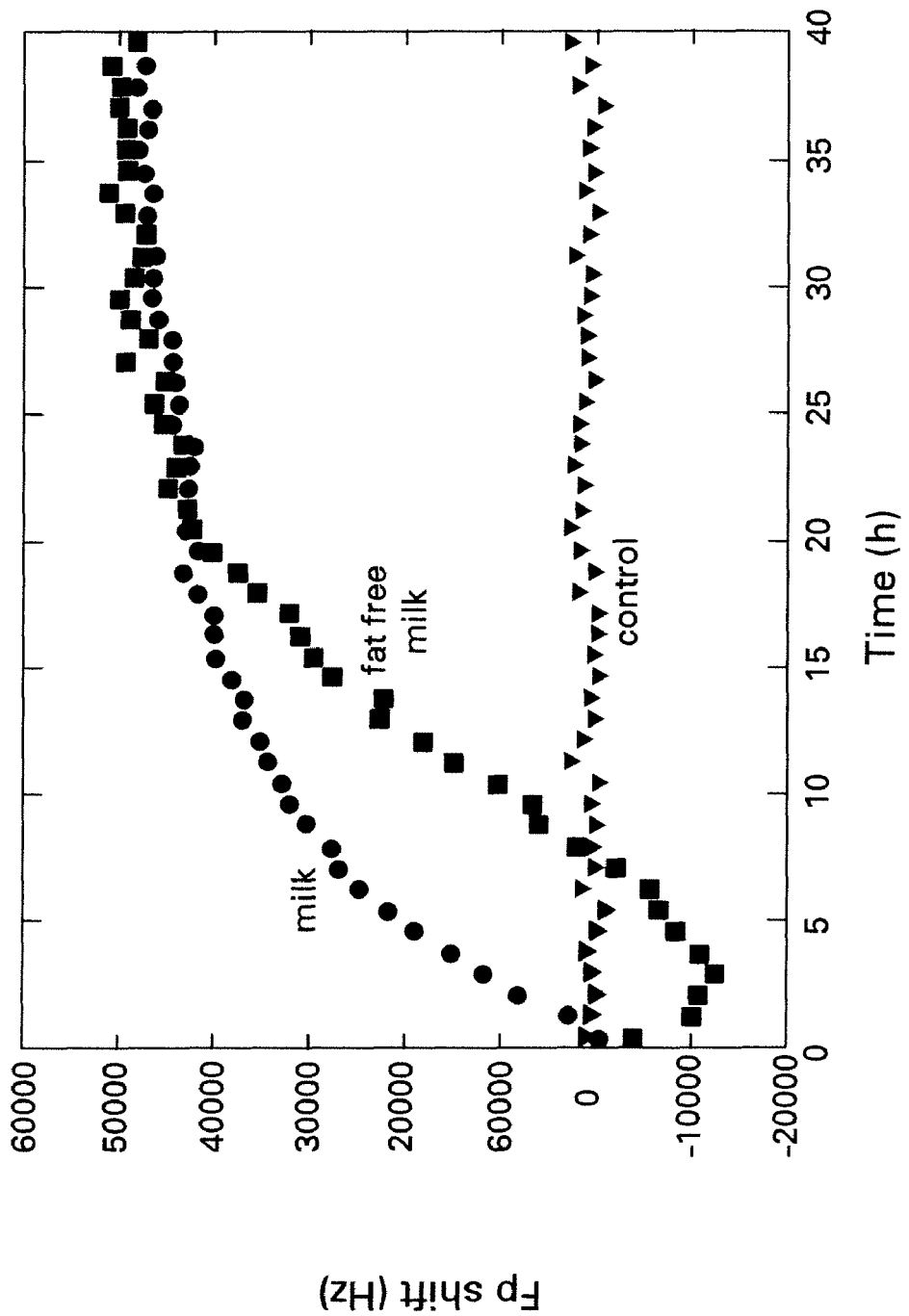

FIG. 23 shows non-invasive monitoring of beverage containers using an embodiment of a disposable RFID sensor.

Figures 24A, 24B:
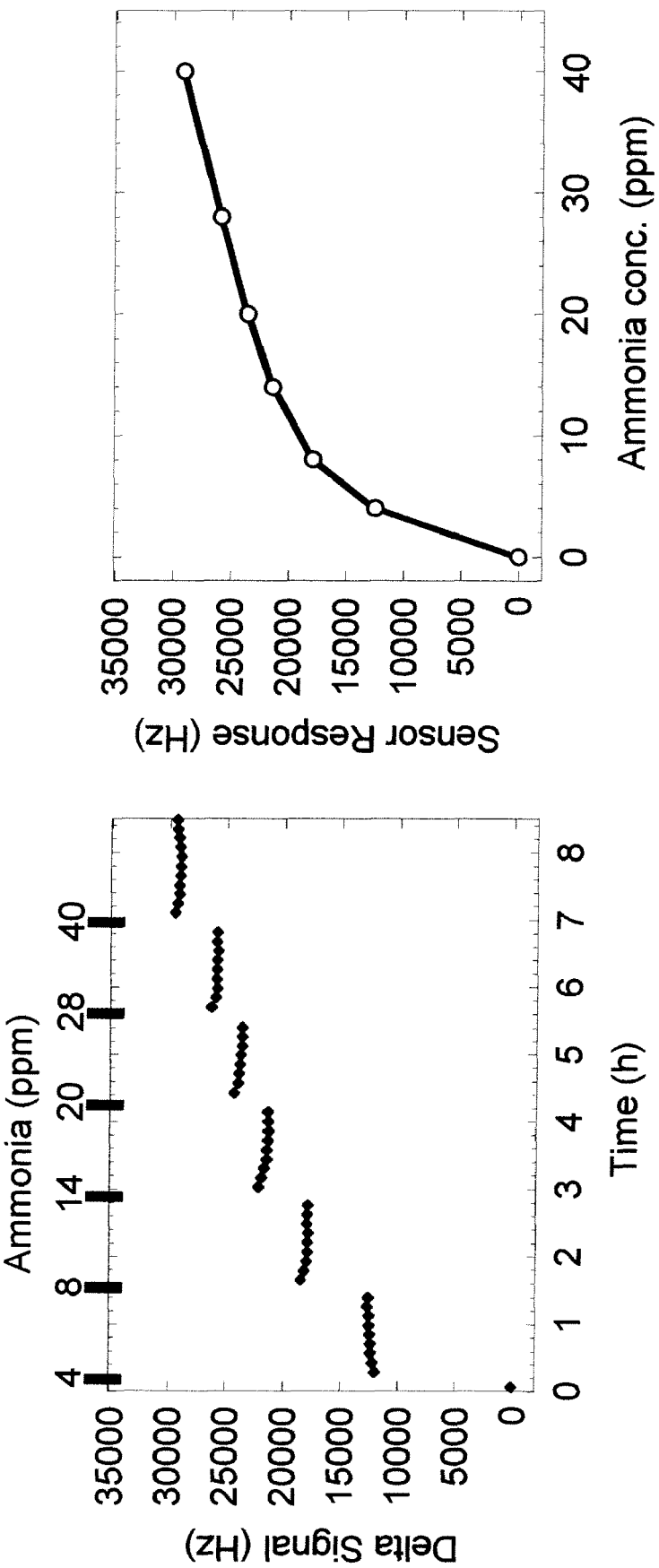

FIG. 24 shows the measured response of an embodiment of an RFID sensor dosimeter for ammonia gas; (A) is an example of a stable signal upon exposure to ammonia gas at different concentrations, and (B) is a calibration curve for the RFID ammonia dosimeter.

FIG. 25 shows improvement in calibrating an embodiment of an RFID sensor using univariate and multivariate calibration analysis.

DETAILED DESCRIPTION

The following detailed description is exemplary and not intended to limit the invention of the application and uses of the invention. Furthermore, there is no intention to be limited by any theory presented in the preceding background of the invention or the following detailed description of the figures.

The embodiments disclosed herein facilitate the calibration of RFID sensors used in manufacturing systems and monitoring systems. Such RFID sensors are adapted to measure a variety of physical, chemical and biological parameters. Each sensor has a digital ID and is calibrated to accurately react to a parameter or parameters of interest through changes in measurements of the sensor's complex impedance. Further, methods are disclosed that enable RFID sensors to be self-calibrated without first exposing the RFID sensors to the parameter of interest.

DEFINITIONS

To more clearly and concisely describe and point out the subject matter of the claimed invention, the following definitions are provided for specific terms, which are used in the following description and the appended claims.

The term "digital ID" includes all data stored in the memory chip of the RFID sensor. Nonlimiting examples of this data are manufacturer identification, user data, and calibrations of the sensor.

The term "monitoring process" includes, but is not limited to, measuring physical changes that occur around the sensor. For example, monitoring processes including monitoring changes in a biopharmaceutical, food or beverage manufacturing process related to changes in physical properties around the sensor. Monitoring processes may also include those industry processes that monitor physical changes as well as changes in a component's composition or position. Nonlimiting examples include homeland security monitoring, residential home protection monitoring, environmental monitoring, clinical or bedside patient monitoring, airport securing, admission ticketing, and public events.

The term "parameters" is used to refer to measurable environmental variables within or surrounding a manufacturing or monitoring system. The measurable environmental variables comprise at least one of physical, chemical and biological properties and include, but are not limited to, measurement of temperature, pressure, material concentration, conductivity, dielectric property, dose of ionizing radiation, light intensity, and environmental conditions.

The term "principal components analysis (PCA)" refers to a mathematical procedure that is used to reduce multidimensional data sets to lower dimensions for analysis. Principal component analysis is also referred to as eigen analysis and may be performed using a covariance matrix or correlation matrix.

The term "protecting material" includes, but is not limited to, materials on the RFID sensor that protect the sensor from an unintended mechanical, physical or chemical effect while still permitting the anticipated measurements to be performed. For example, an anticipated measurement may include solution conductivity measurement wherein a protecting film separates the sensor from the liquid solution yet allows an electromagnetic field to penetrate into solution. An example of a protecting material is a paper film that is applied on top of the sensor to protect the sensor from mechanical damage and abrasion. Another example of a protecting material is a polymer film that is applied on top of the sensor to protect the sensor from corrosion when placed in a liquid for measurements. A protecting material may also be a polymer film that is applied on top of the sensor for protection from shortening of the sensor's antenna circuit when placed in a conducting liquid for measurements. Non-limiting examples of protecting films are paper and polymeric films such as polyesters, polypropylene, polyethylene, polyethers, polycarbonate, and polyethylene terepthalate.

As used herein the term "sensing materials and sensing films" includes, but is not limited to, materials deposited onto the RFID sensor to perform the function of predictably and reproducibly affecting the complex impedance sensor response upon interaction with the environment. For example, a conducting polymer such as polyaniline changes its conductivity upon exposure to solutions of different pH. When such a polyaniline film is deposited onto the RFID sensor, the complex impedance sensor response changes as a function of pH. Thus, such an RFID sensor works as a pH sensor. When such a polyaniline film is deposited onto the RFID sensor for detection in gas phase, the complex impedance sensor response also changes upon exposure to basic (for example, $NH_3$) or acidic (for example HCl) gases. Sensor films include, but are not limited to, polymer, organic, inorganic, biological, composite, and nano-composite films that change their electrical and or dielectric property based on the environment that they are placed in. Non-limiting additional examples of sensor films may be a sulfonated polymer such as Nafion, an adhesive polymer such as silicone adhesive, an inorganic film such as sol-gel film, a composite film such as carbon black-polyisobutylene film, a nanocomposite film such as carbon nanotube-Nafion film, gold nanoparticle-polymer film, metal nanoparticle-polymer film, electrospun polymer nanofibers, electrospun inorganic nanofibers, electrospun composite nanofibers, and any other sensor material. In order to prevent the material in the sensor film from leaking into the liquid environment, the sensor materials are attached to the sensor surface using standard techniques, such as covalent bonding, electrostatic bonding and other standard techniques known to those of ordinary skill in the art.

As used herein the term "RFID tag" refers to a data storage and reporting technology that uses electronic tags for storing data and which contains at least two components where the first component is an integrated circuit (memory chip) for storing and processing information and modulating and demodulating a radio frequency signal. This memory chip can also be used for other specialized functions, for example it can contain a capacitor. It can also contain an input for an analog signal. The second component is an antenna for receiving and transmitting the radio frequency signal.

The term "RFID sensor" is any RFID tag with an added sensing function as, for example, when an antenna of the RFID tag also performs sensing functions by changing its complex impedance parameters as a function of environmental changes. The accurate determinations of environmental changes with such RFID sensors are performed by analysis of complex impedance. RFID tags are converted into RFID sensors also by attaching a complementary sensor across antenna and or/memory chip. By attaching such a sensor, electrical response of the attached sensor is translated into simultaneous change of complex impedance response, resonance peak position, peak width, peak height and peak symmetry of the complex impedance response of the sensor antenna, magnitude of the real part of the complex impedance, resonant frequency of the imaginary part of the complex impedance, antiresonant frequency of the imaginary part of the complex impedance, zero-reactance frequency, phase angle, and magnitude of impedance.

The term "single-use component" includes, but is not limited to, manufacturing or monitoring equipment, and packaging, which may be disposed of after use or reconditioned for reuse. Single use manufacturing components include, but are not limited to, single-use vessels, bags, chambers, tubing, connectors, and columns. Single-use packaging in the food industry includes but is not limited to food and drinks packaging, candy and confection boxes. Single-use monitoring components include, but are not limited to, single-use cartridges, dosimeters, and collectors.

The term "writer/reader" includes, but is not limited to, a combination of devices to write and read data into the memory of the memory chip and to read impedance of the antenna.

Methods

A passive RFID tag does not need a battery for its function and comprises a memory microchip, which is connected to an antenna coil for communication with a writer/reader. The microchip can be read by illuminating the tag by a radio frequency (RF) carrier signal sent by the writer/reader. When the RF field passes through an antenna coil, an AC voltage is generated across the coil. This voltage is rectified in the microchip to result in a DC voltage for the microchip operation. The microchip becomes functional when the DC voltage reaches a predetermined level. By detecting the RF signal backscattered from the microchip, the information stored in the microchip can be fully identified. The distance between the passive tag and the writer/reader is governed by the design parameters that include operating frequency, RF power level, writer/reader's receiving sensitivity, antenna dimensions, data rate, communication protocol, and microchip power requirements. The communication distance between writer/reader and tag is typically limited within a proximity distance because the passive tag operates with only microwatts of RF power from the writer/reader. For passive tags operating at 13.56 MHz, the read distance is typically not more than several centimeters. The typical frequency range of operation of 13.56 MHz passive RFID tags for digital ID writing/reading is from 13.553 to 13.567 MHz. The typical frequency range of operation of 13.56-MHz passive RFID sensors for sensing of environmental changes around the RFID sensor is from about 5 MHz to about 20 MHz, more preferably from 10 to 15 MHz. The requirement for this frequency range is to be able to recognize the tag with writer/reader that operates at 13.56 MHz while the sensor portion of the RFID tag operates from 5 to 20 MHz. To not exceed regulatory electromagnetic emission requirements, RFID sensors are designed to operate at low RF power levels Depositing sensing films onto passive RFID tags creates RFID chemical, biological, or physical sensors. RFID sensing is performed by measuring changes in the RFID sensor's complex impedance as a function of physical changes around the sensor. Examples of physical changes include, but are not limited to, temperature, pressure, conductivity, and dielectric properties. If the frequency response of the antenna coil, after deposition of the sensing film, does not exceed the frequency range of operation of the tag, the information stored in the microchip can be identified with a conventional RFID writer/reader. Similarly, an impedance analyzer can read the complex impedance of the antenna coil to correlate the changes in complex impedance to the chemical and biological species of interest and to physical changes around the sensor.

Figure 1:
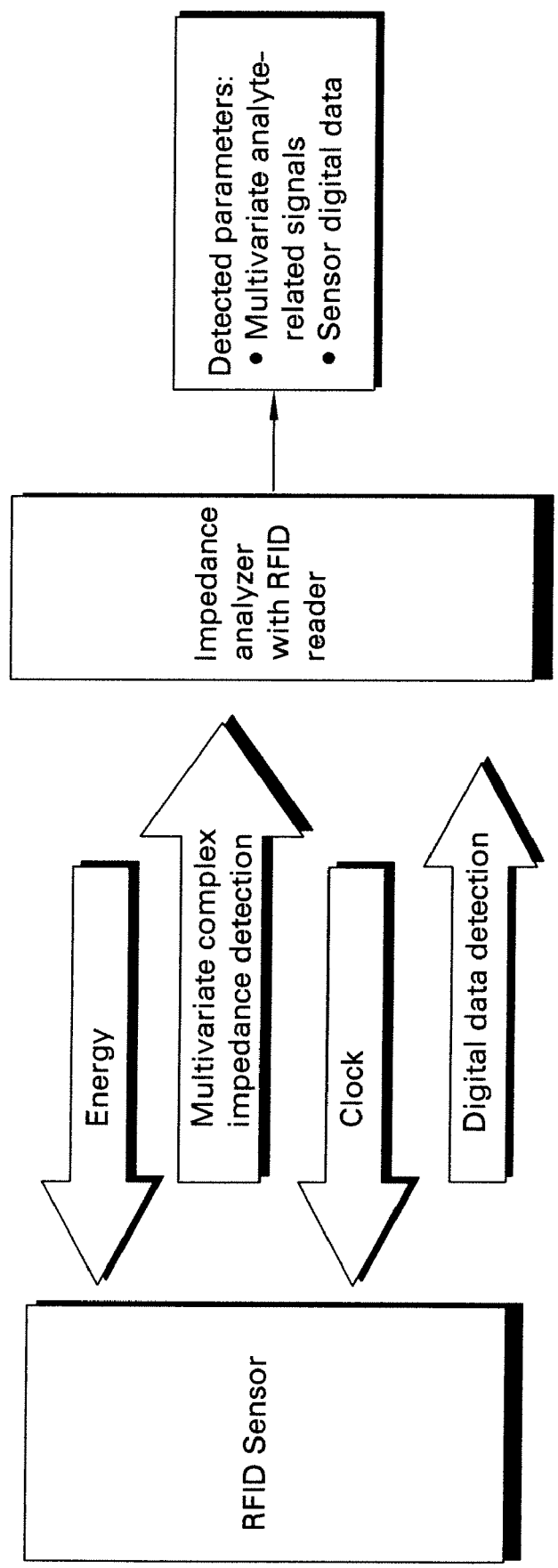
FIG. 1 illustrates the operation of an embodiment of an RFID sensor.

FIG. 1 illustrates the operation of an embodiment of an RFID sensor. Upon coating of the RFID tag with a chemically sensitive film, or by simply using an RFID tag for physical sensing, or by attaching a complementary sensor to the antenna, both the digital tag ID and the complex impedance of the tag antenna are measured. The measured digital ID provides information about the identity of the tag itself, such as an object onto which this tag is attached, and the properties of the sensor (e.g. calibration curves for different conditions, manufacturing parameters, expiration date, etc.). For multi-component detection, multiple properties from the measured real and imaginary portions of the complex impedance of a single RFID sensor may be determined.

Figure 2:
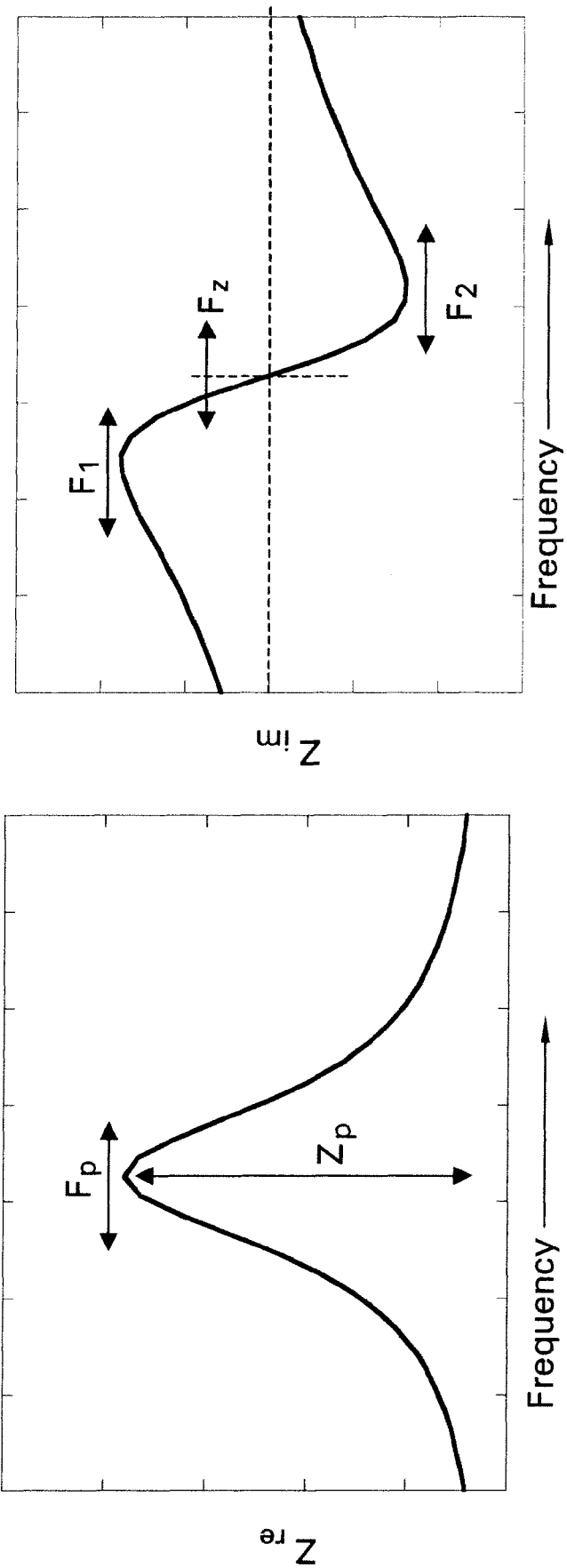
FIG. 2 illustrates an example of measured responses of an exemplary RFID sensor (full complex impedance spectra, Fp, Zp, Fz, F1, and F2).

FIG. 2 illustrates an example of measured responses of an exemplary RFID sensor, which includes the sensor's full complex impedance spectra and several individually measured properties Fp, Zp, Fz, F1 and F2. These properties include the frequency of the maximum of the real part of the complex impedance (Fp, resonance peak position), magnitude of the real part of the complex impedance (Zp, peak height), zero-reactance frequency (Fz, frequency at which the imaginary portion of impedance is zero), resonant frequency of the imaginary part of the complex impedance (F1), and antiresonant frequency of the imaginary part of the complex impedance (F2). The difference between F1 and F2 is related to peak width. Since F1 and F2 are related to different components of an equivalent circuit, F1 and F2 are not correlated. Therefore peak symmetry is affected by changes in complex impedance. Other parameters can be measured using the entire complex impedance spectra, for example, quality factor of resonance, phase angle, and magnitude of impedance. Measurement of the entire spectra results in improved accuracy and precision of calibration.

When an RFID sensor contains a complementary sensor across an antenna and memory chip, the electrical response of the attached complementary sensor is translated into changes in the complex impedance response of the antenna, resonance peak position, peak width, peak height and peak symmetry of the complex impedance response of the antenna. The attached complementary sensor is not connected to the analog input of the memory chip and does not change the digital information content on the memory chip of the RFID sensor. The complementary sensor of this invention changes the antenna complex impedance and does not introduce a signal to the memory chip.

Figure 3:
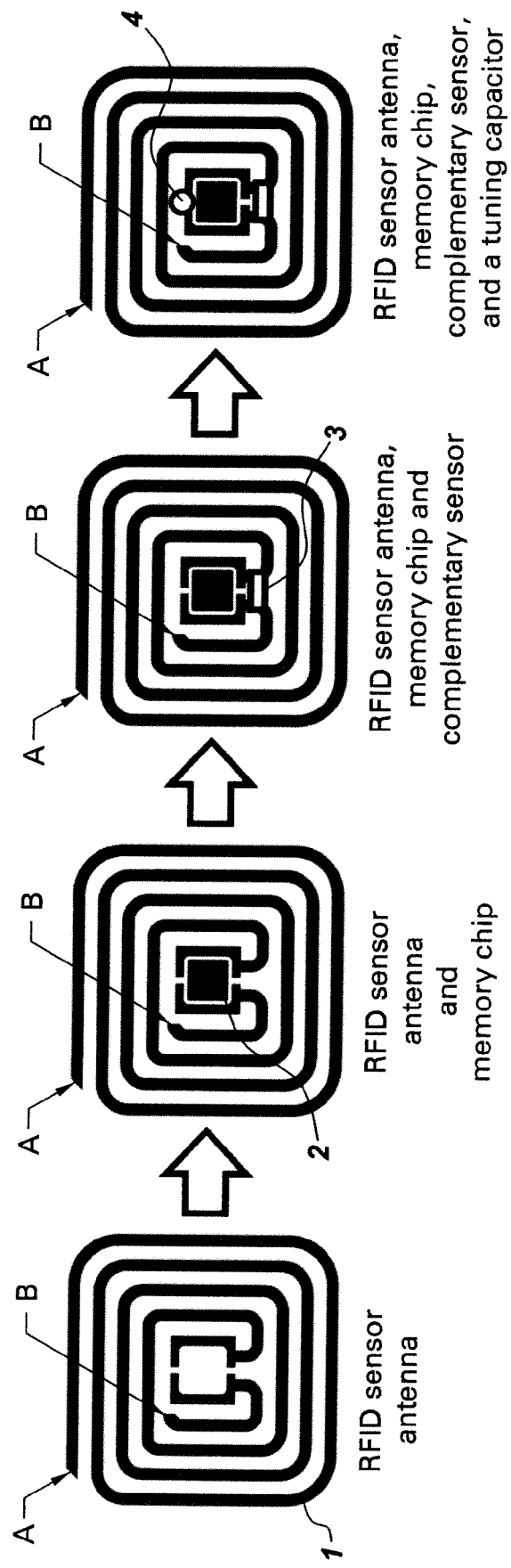
FIG. 3 illustrates an embodiment of a process for the fabrication of an RFID sensor.

FIG. 3 illustrates an embodiment of a process for the fabrication of an RFID sensor with a complementary sensor. An antenna 1 of an RFID sensor is fabricated. The ends A and B on the antenna are electrically connected using a conductor medium (such as a conductor wire, a conductor strip, or a conductor cable) in such a way that the conductor medium does not electrically shorten the other regions of the antenna that this conductor medium crosses. A memory chip 2 is galvanically attached to the antenna. The chip is used for storing digital information (digital ID). The memory chip operates over at least one of the assigned radio frequency regions in the range from about 100 kHz to about 1 GHz. The chip 2 is activated by the radio frequency signal transmitted from the read/write unit. A complementary sensor 3 is attached to the antenna 1. The electrical response of the attached complementary sensor is translated into changes in the complex impedance response of the antenna, resonance peak position, peak width, peak height and peak symmetry of the complex impedance response of the antenna, magnitude of the real part of the complex impedance, resonant frequency of the imaginary part of the complex impedance, antiresonant frequency of the imaginary part of the complex impedance, quality factor of resonance, zero-reactance frequency, phase angle, and magnitude of impedance. The attached complementary sensor is not connected to the analog input of the memory chip and does not change the digital information content on the memory chip of the RFID sensor. The complementary sensor of this invention changes the antenna complex impedance and does not introduce a signal to the memory chip. The RFID sensor with the complementary sensor 3 can also have a tuning capacitor 4 attached to antenna 1. The electrical response of the sensor may be characterized as one of seven types (1) preferential resistance change, (2) preferential capacitance change, (3) preferential inductance change, (4) simultaneous resistance and capacitance change, (5) simultaneous inductance and capacitance change, (6) simultaneous resistance and inductance change, or (7) simultaneous resistance, inductance and capacitance change. Nonlimiting examples of RFID complementary sensors are thermistors, vapor-responsive chemoresistors, water conductivity sensors, immunosensing conductivity sensors, aptamer-based conductivity sensors, interdigital electrode sensor structures filled with materials with variable dielectric property, immunosensing interdigital electrode sensors, aptamer-based interdigital electrode sensors.

Figure 4:
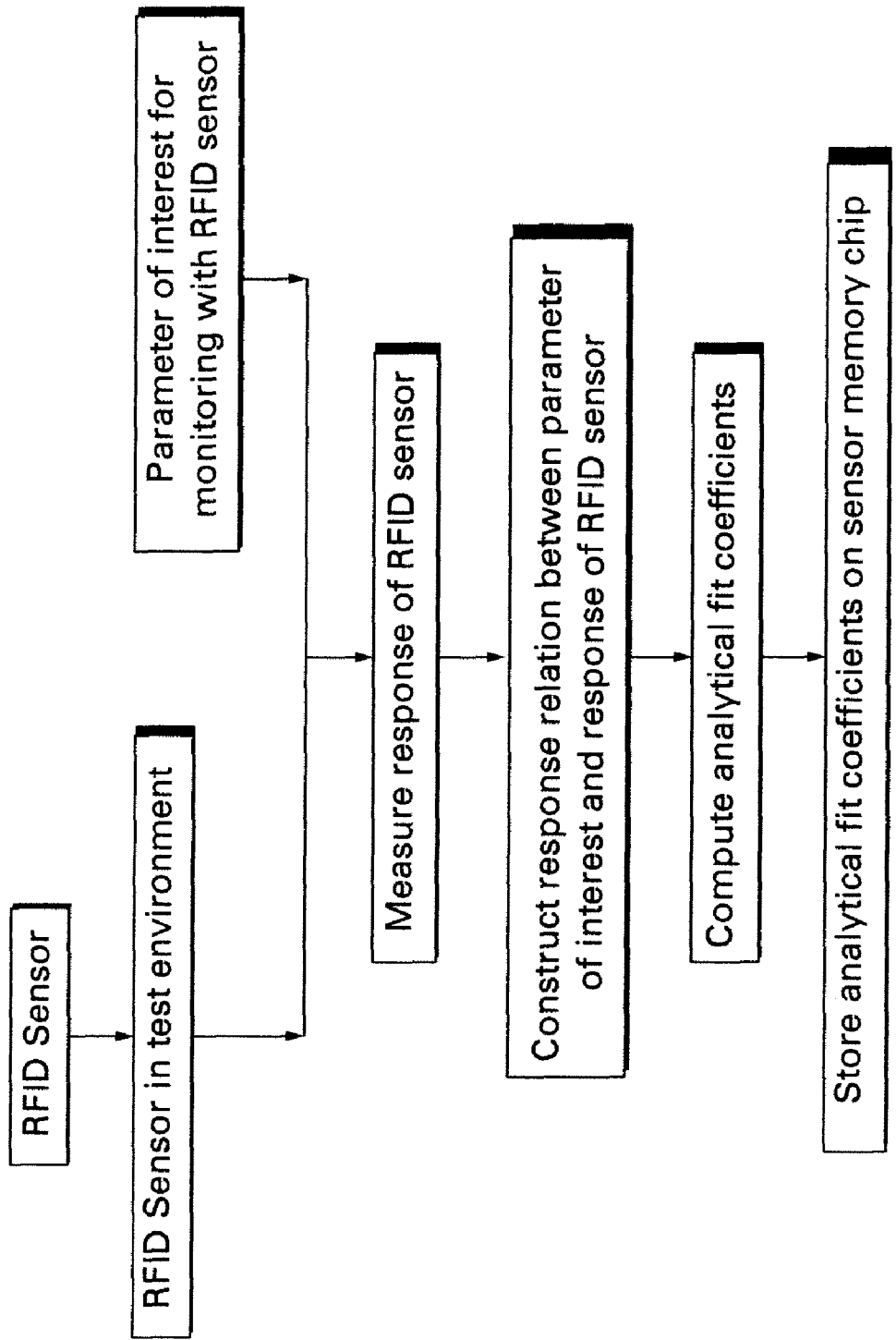
FIG. 4 shows a block diagram of the calibration steps of an embodiment of an RFID sensor.

FIG. 4 is a block diagram illustrating the calibration steps of an embodiment of an RFID sensor. For sensor calibration, at least one sensor is positioned into a test environment such as a test chamber or a disposable biocomponent. For multiple sensors, positioning and calibration in the test environment can occur simultaneously or sequentially. One or more sensors are exposed to at least one environmental parameter at a predetermined level such as temperature, solution conductivity, vapor concentration, or biological material concentration. The response of the one or more sensors is measured and an analytical relationship between the environmental parameter and the sensor response is established. If needed, responses of the sensor to more than one value of the environmental parameter of interest are collected. Analytical fit coefficients are computed which relate sensor response to the environmental parameter. The resulting analytical fit coefficients are stored in the memory chip of the RFID sensor.

The analytical fit coefficients are calculated using univariate calibration or a multivariate calibration. In univariate calibration, a single property of the sensor response, for example, change in Zp or change in Fp, Fz, F1, and F2 is related to the environmental parameter, for example temperature. In multivariate calibration, more than one property of the sensor response is related to the value of the environmental parameter of interest. Multivariate calibration utilizes the full complex impedance spectra for calibration, or at least two of individually measured parameters (Zp, Fp, Fz, F1, F2), or at least two of any other parameters that can be extracted from the response of the resonance circuit of the RFID sensor. Nonlimiting examples of these additional parameters are quality factor of resonance, phase angle, and magnitude of impedance of the resonance circuit response of the RFID sensor. Nonlimiting examples of multivariate analysis tools are canonical correlation analysis, regression analysis, non-linear regression analysis principal components analysis, discriminate function analysis, multidimensional scaling, linear discriminate analysis, logistic regression, and/or neural network analysis.

Figure 5:
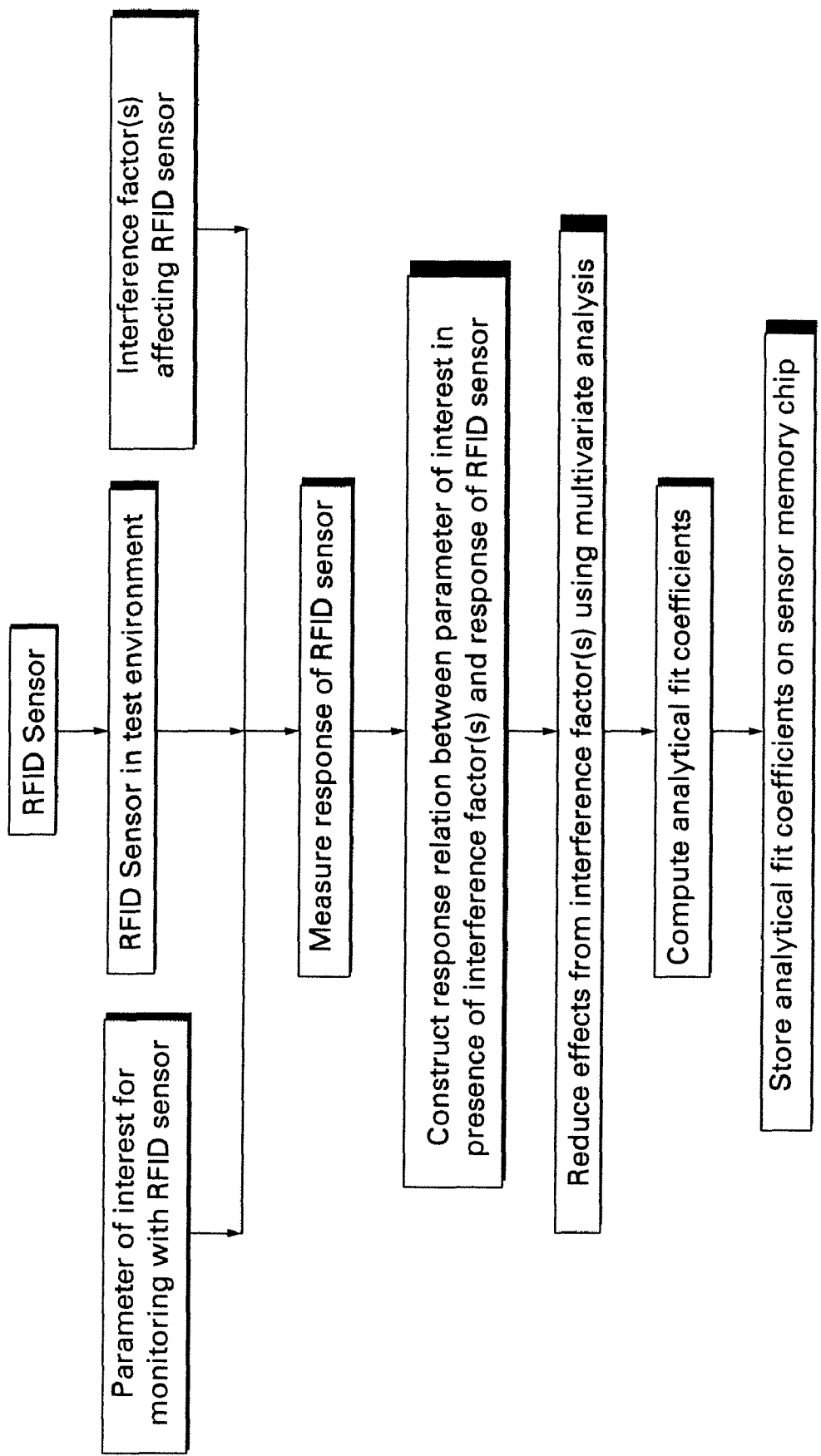
FIG. 5 shows a block diagram of calibration steps of an embodiment of an RFID sensor with anticipated presence of interferences.

FIG. 5 is a block diagram illustrating the calibration steps of an embodiment of an RFID sensor with anticipated interferences. For sensor calibration, the sensor is positioned into a test environment such as a test chamber. Either a single sensor or multiple sensors can be positioned and calibrated in the test environment. The sensor is exposed to at least one environmental parameter of interest at a predetermined single level or more than one level and at least one interference factor. For example, solution conductivity may be the environmental parameter of interest while temperature variations of a solution may be the interference factor.

Analytical fit coefficients are computed that relate sensor response, parameter value, and interference value. The analytical fit coefficients are stored into the memory of the RFID sensor. Thus, upon using the RFID sensor in a subsequent application in a manufacturing or a monitoring process, the analytical fit coefficients are read from the memory chip of the sensor. The sensor response is collected upon exposure to its environment, the value of the sensor response is converted into the value of the parameter of interest using the stored analytical fit coefficients and the computed value of the parameter is sent to a display device or to a control device or stored back into the memory of the memory chip of the RFID sensor. The storage of this data is performed by using a reader/writer device.

Alternatively, the calibration of an RFID sensor may be performed without exposing the sensor to samples that contain an analyte or an interference factor. Instead, at least one material (solid, gel, powder, liquid, etc.) with well-defined dielectric or other desired properties is used. This material is placed in proximity to the RFID sensor and the response of the sensor to this material is recorded. A prior established correlation between the sensor response to this material and a real sample containing the analyte or interference factor is used for calibration. More than one material may be used to obtain several calibration points.

Figure 6:
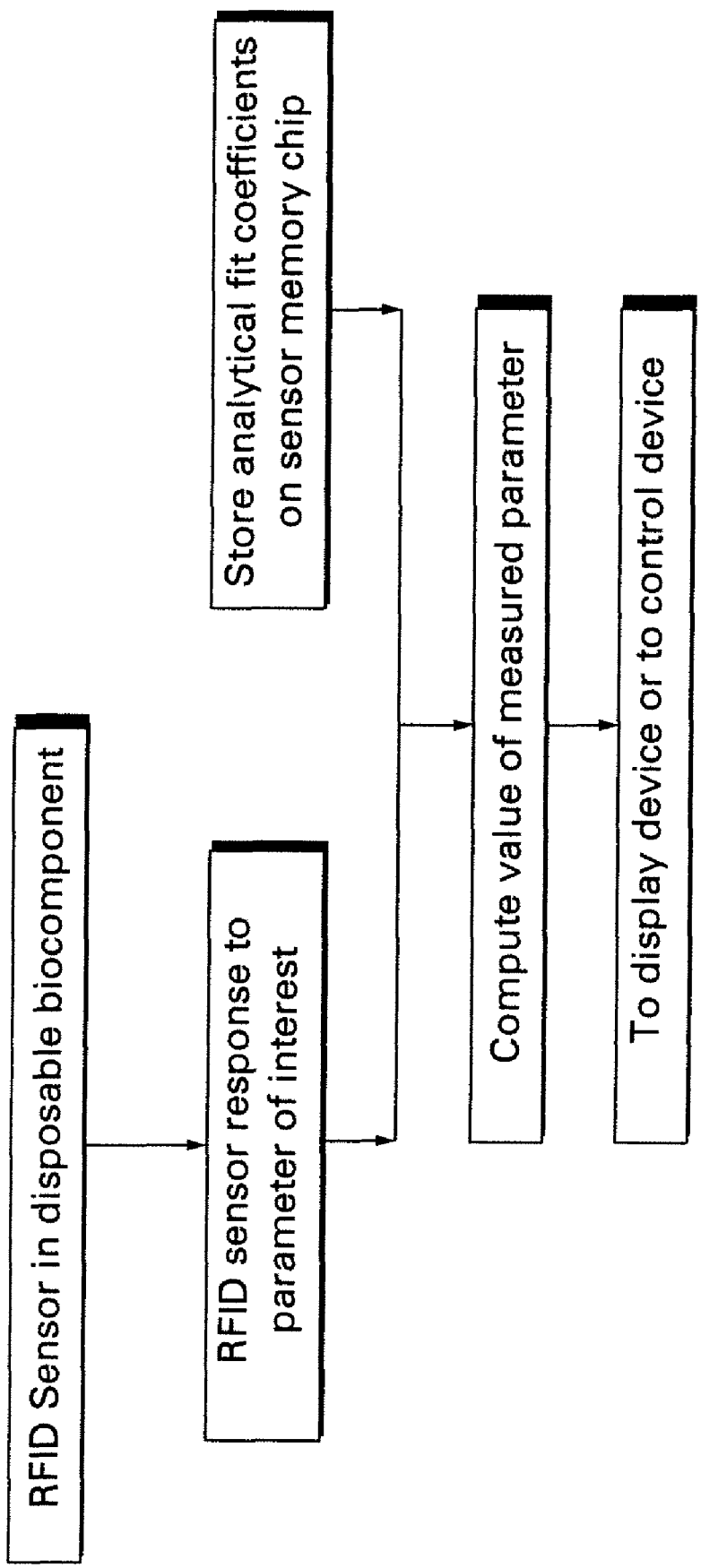
FIG. 6 is a block diagram illustrating an embodiment of a calibration process for an RFID sensor incorporated into a disposable biocomponent.

FIG. 6 is a block diagram illustrating an embodiment of a calibration process for an RFID sensor incorporated into a disposable biocomponent. As shown, in a manufacturing or a monitoring process application, stored analytical fit coefficients are read from the memory chip of an RFID sensor. The sensor response is collected upon exposure to the environment, the value of the sensor response is converted into the value of the environmental parameter of interest using analytical fit coefficients, and the computed environmental value is sent to a display device or to a control device or stored back into the memory of the memory chip of the RFID sensor. The storage of this data is performed by using a reader/writer device.

Figure 7:
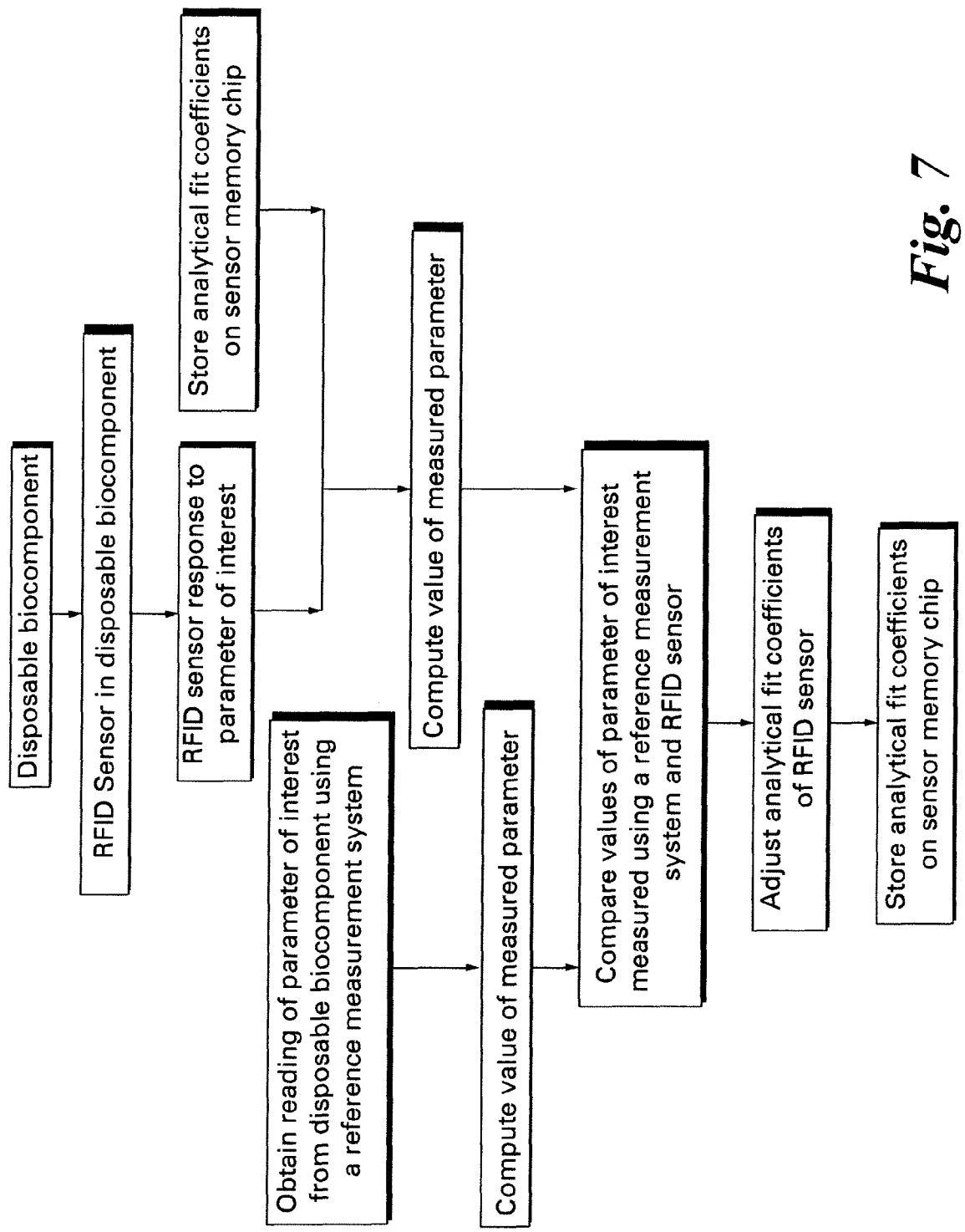
FIG. 7 is a block diagram illustrating an embodiment of a periodic validation and calibration process for an RFID sensor incorporated into a disposable biocomponent.

FIG. 7 is a block diagram illustrating an embodiment of a periodic validation and calibration process for an RFID sensor incorporated into a disposable biocomponent. As shown, in a manufacturing or monitoring process, stored analytical fit coefficients of an RFID sensor are read from the memory chip of the sensor. The sensor response is collected upon exposure to the environment, the value of the sensor response is converted into the value of the environmental parameter of interest using analytical fit coefficients, and the computed environmental parameter value is obtained.

To validate the calibration of the RFID sensor incorporated into a disposable biocomponent, the environmental parameter of interest is measured using a reference measurement system. For example, in Wave Biotech disposable bioreactors from GE Healthcare, a sample port is available for aseptic sampling of a liquid from the bioreactor to validate the calibration of sensors. Using the reference measurement system, a value of measured environmental response is determined and the calibration value is compared to the value obtained from the RFID sensor. If these two values differ more than the measurement precision, the analytical fit coefficients of the RFID sensor are adjusted and the new coefficients are written into the RFID sensor memory chip.

Example 1

Calibration Based on Measurements of Complex Impedance

Passive 13.56 MHz RFID tags (Texas Instruments) were used for temperature sensing and for demonstration of the disclosed calibration methods. Digital ID of the RFID sensors was read with a Skytek reader. Seven RFID sensors were used with the read IDs shown in Table 1.

TABLE 1

Digital IDs of the employed RFID sensors

| Sensor Number | Digital ID | Comments |
|---|---|---|
| S1 | E007 000 0219 24E9 | Replicate measurements (n = 4) of temperature response |
| S2 | E007 000 0219 24E8 | Replicate measurements (n = 2) of temperature response |
| S3 | E007 000 0219 24E3 | No complex impedance measurements done |
| S4 | E007 000 0219 24E7 | Replicate measurements (n = 2) of temperature response, used for blind calibration |
| S5 | E007 000 0219 24E5 | Replicate measurements (n = 2) of temperature response |

TABLE 1-continued

Digital IDs of the employed RFID sensors

| Sensor Number | Digital ID | Comments |
|---|---|---|
| S6 | E007 000 0219 24DA | Replicate measurements (n = 2) of temperature response |

Measurements of the complex impedance of the RFID sensor were performed with a network analyzer (Model E5062A, Agilent Technologies) and a laptop computer. The network analyzer was used to scan the frequencies over the range of interest and to collect the complex impedance response from the tag. The data was collected using LabVIEW software and analyzed using KaleidaGraph (Synergy Software, Reading, Pa.) and PLS_Toolbox (Eigenvector Research, Inc., Manson, Wash.) operated with Matlab (The Mathworks Inc., Natick, Mass.).

Figure 8:
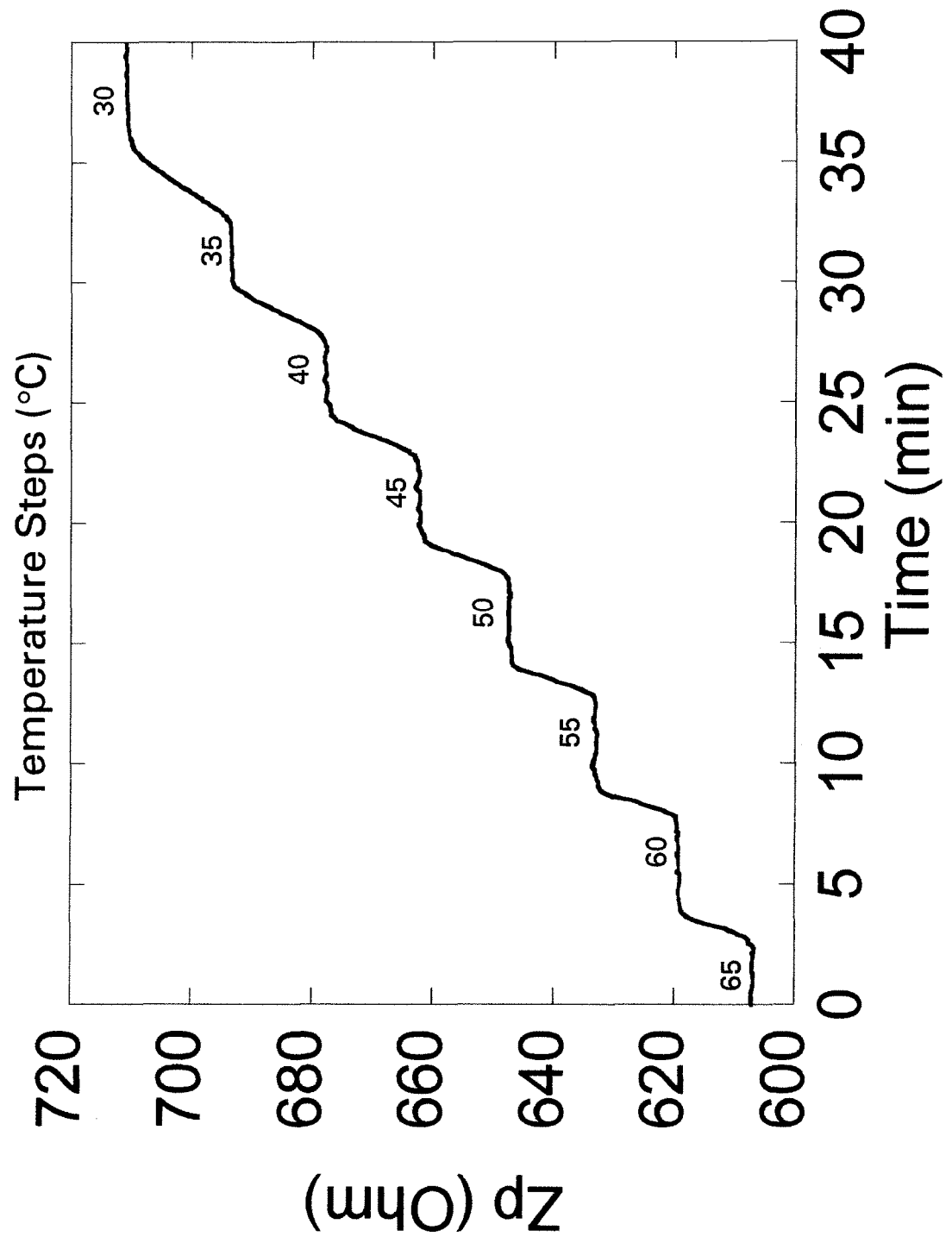
FIG. 8 illustrates an example of a temperature response of an embodiment of an RFID sensor (sensor S1).
Figure 9A:
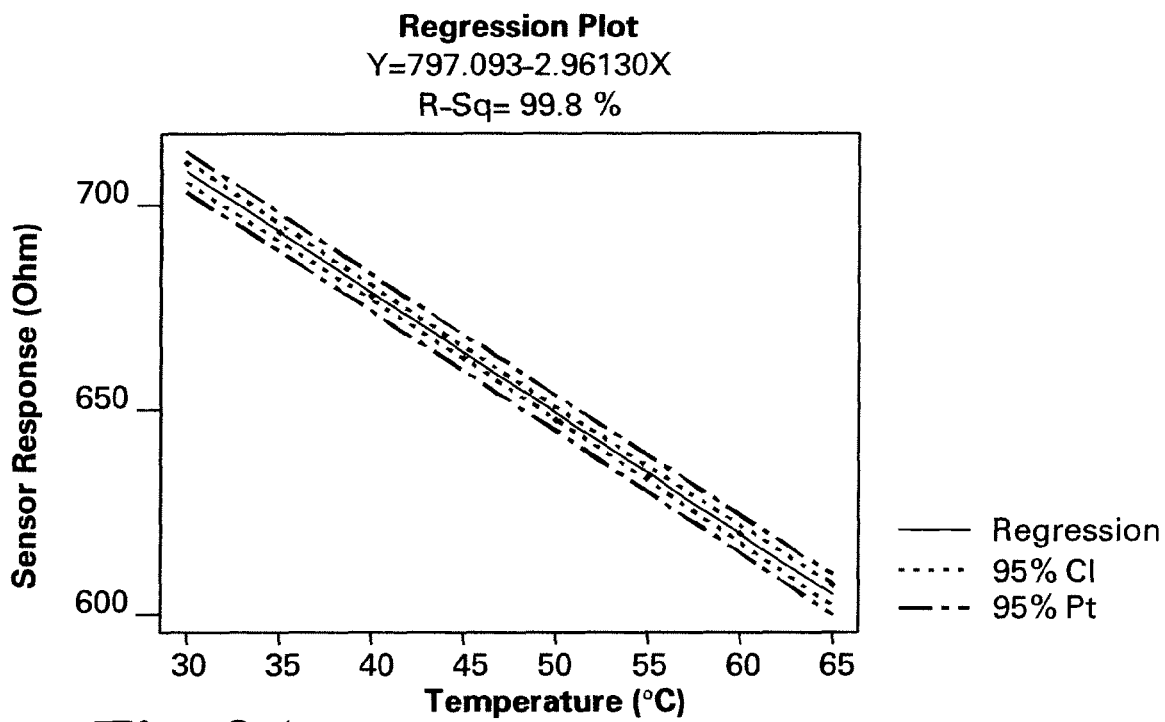
FIG. 9 shows the prediction of temperature response from an embodiment of a single RFID sensor S1: (A) linear fit, (B) quadratic fit.
Figure 9B:
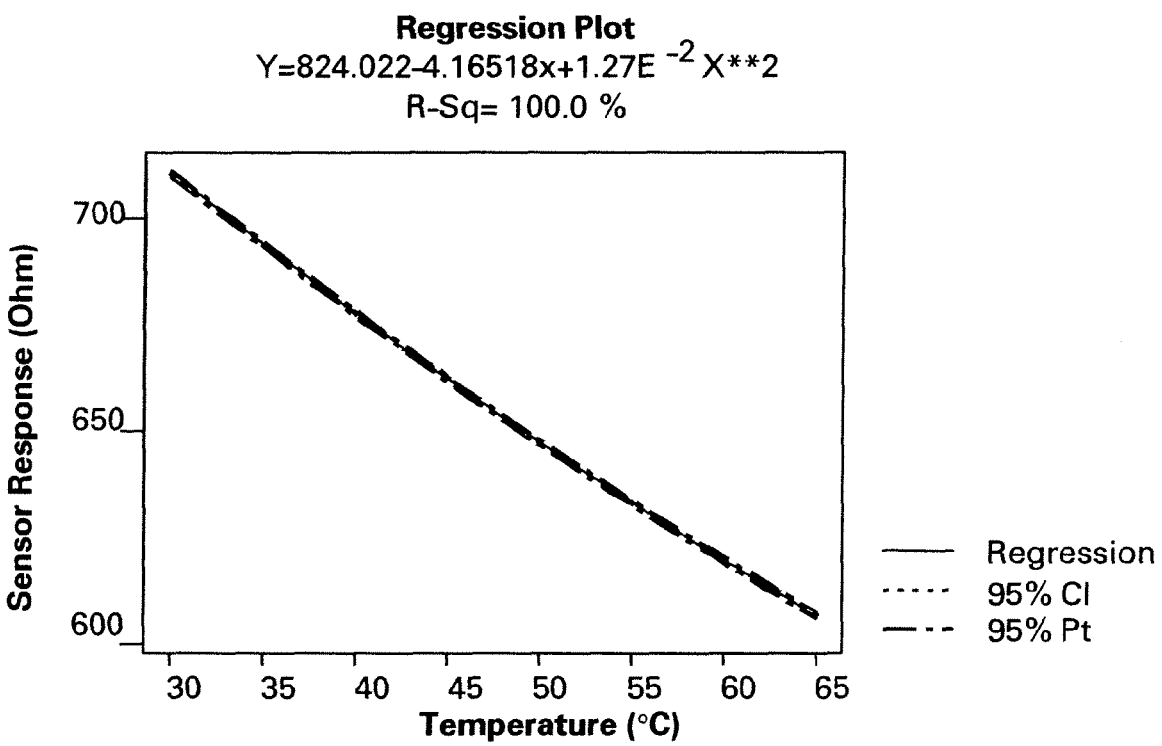

To construct calibration curves, F1, F2, Fp, and Zp parameters of the complex impedance of the RFID sensors were measured as a function of time upon step changes in temperature ranging from 65 to 30° C. A typical temperature response of one of the RFID sensors is presented in FIG. 8, which demonstrates a reproducible temperature response of an embodiment of an RFID sensor, S1. Prediction of temperature response from a single RFID sensor, S1, is presented in FIGS. 9A and 9B. Linear and quadratic fits of the experimental data show the improvement of predicted temperature values using a quadratic fit compared to a linear fit.

Calibration of different RFID sensors was achieved based on the initial value of the measured parameter of the complex impedance. Table 2 shows calibration values, Fp, for each sensor obtained by measuring RFID sensor response at a given temperature (such as 30° C.). For sensor calibration, the Fp values were subtracted from the readings of the RFID sensors. Thus, the initial readings after calibration at 30° C. were zero (see FIG. 10B). In this embodiment, because the calibration was done at a single temperature, the calibration is referred to as a single point calibration.

TABLE 2

Calibration Fp values for each sensor

| Sensor Number | Measured Digital ID | Replicate measurements of $Z_{re}$ and $Z_{im}$ | Calibration Fp value (MHz) at 30° C. |
|---|---|---|---|
| S1 | E007 000 0219 24E9 | 1 | 13100997 |
| S1 | Same | 2 | 13105310 |
| S1 | Same | 3 | 13107915 |
| S1 | Same | 4 | 13108030 |
| S2 | E007 000 0219 24E8 | 1 | 13101750 |
| S2 | Same | 2 | 13106773 |
| S3 | E007 000 0219 24E3 |  | NA |
| S4 | E007 000 0219 24E7 | 1 | 13106042 |
| S4 | Same | 2 | 13118595 |
| S5 | E007 000 0219 24E5 | 1 | 13103802 |
| S5 | Same | 2 | 13109270 |
| S6 | E007 000 0219 24DA | 1 | 13090937 |
| S6 | Same | 2 | 13096320 |

Figure 10A:
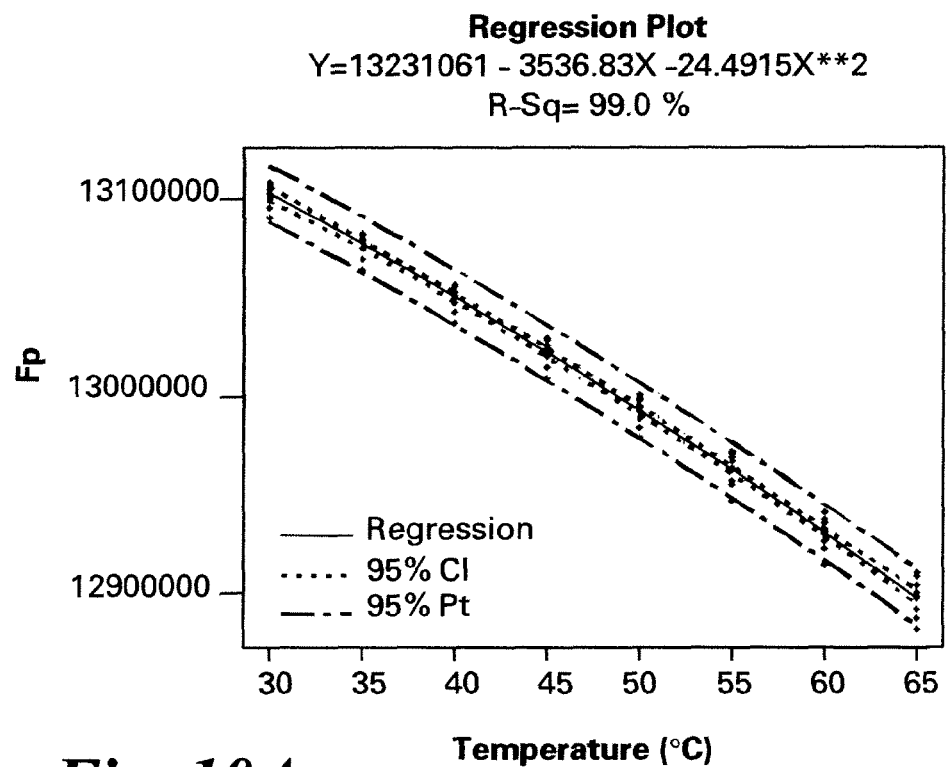
FIG. 10 shows the measured responses of RFID sensors: (A) before calibration and (B) after calibration.

FIG. 10A graphically shows the data points collected from four tested sensors done in replicates and without calibration. FIG. 10A has 80 data points (8 temperature values per sensor x (S1×4 replicates)×(S2×2 replicates)×(S5×2 replicates)× (S6×2 replicates). The data points were used to construct a temperature prediction model based on quadratic regression:

$Y=13231061-3536.83X-24.4915X^2$ with a R-Sq value of 99.0%. In FIG. 10A, dashed lines above and below the data points show the confidence interval for predicting Fp from the measured values. "CI" in FIGS. 10A and 10B refers to "confidence interval" and "PI" refers to "prediction interval".

Figure 10B:
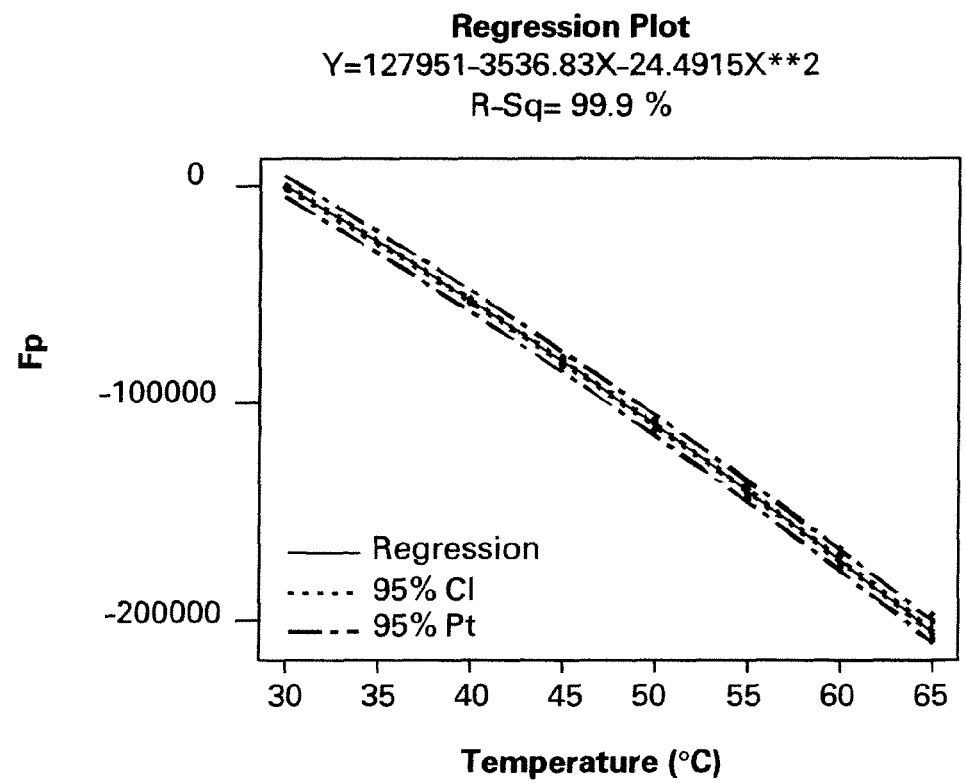

FIG. 10B shows the response of the RFID sensors after a single point calibration process at 30° C. The temperature prediction model based on a quadratic equation yielded $Y=127951-3536.83X-24.4915X^2$ with an R-Sq value of 99.9%. After calibration, the spread of predicted temperatures from the measured Fp values from the RFID sensors (indicated with dashed lines above and below the data points) is reduced from the non-calibrated sensors shown in FIG. 10A. The results show the ability of RFID sensors to accurately measure temperature is significantly improved using calibration.

Figure 11A:
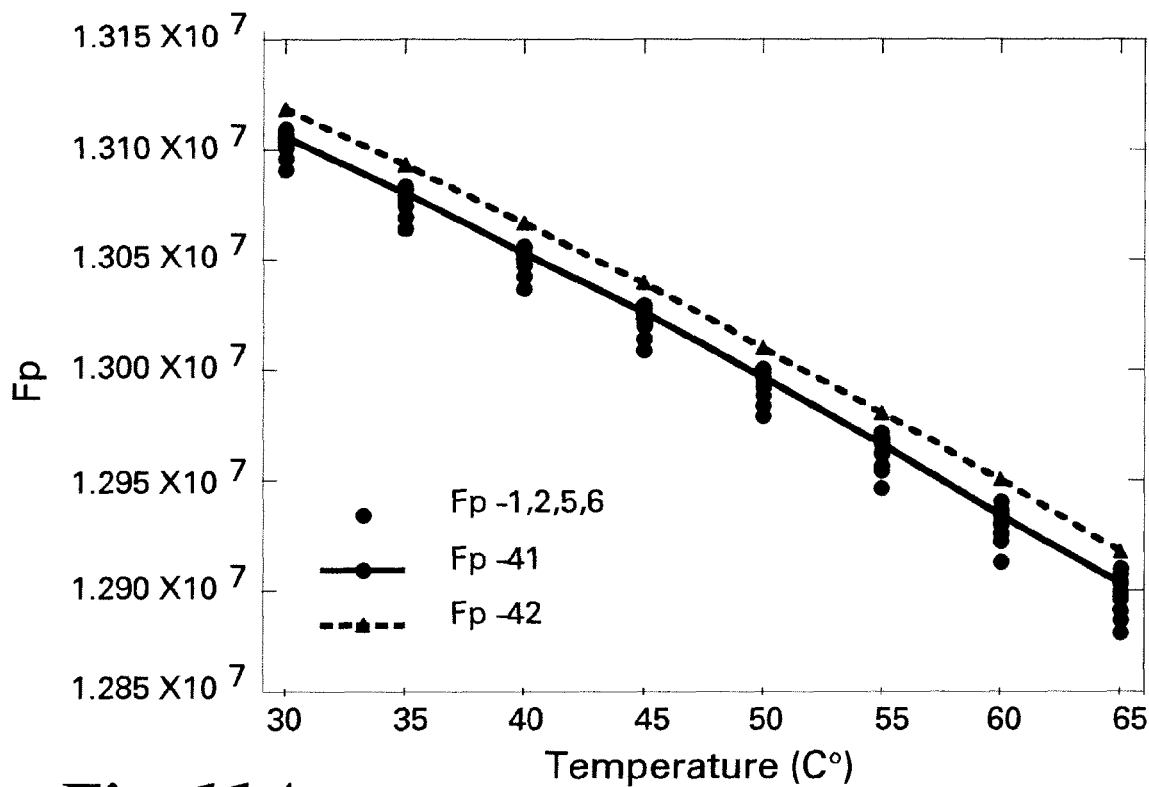
FIG. 11 shows the variation in the measured response of an embodiment of an RFID sensor exposed to different temperatures: (A) prior to calibration and (B) after calibration.
Figure 11B:
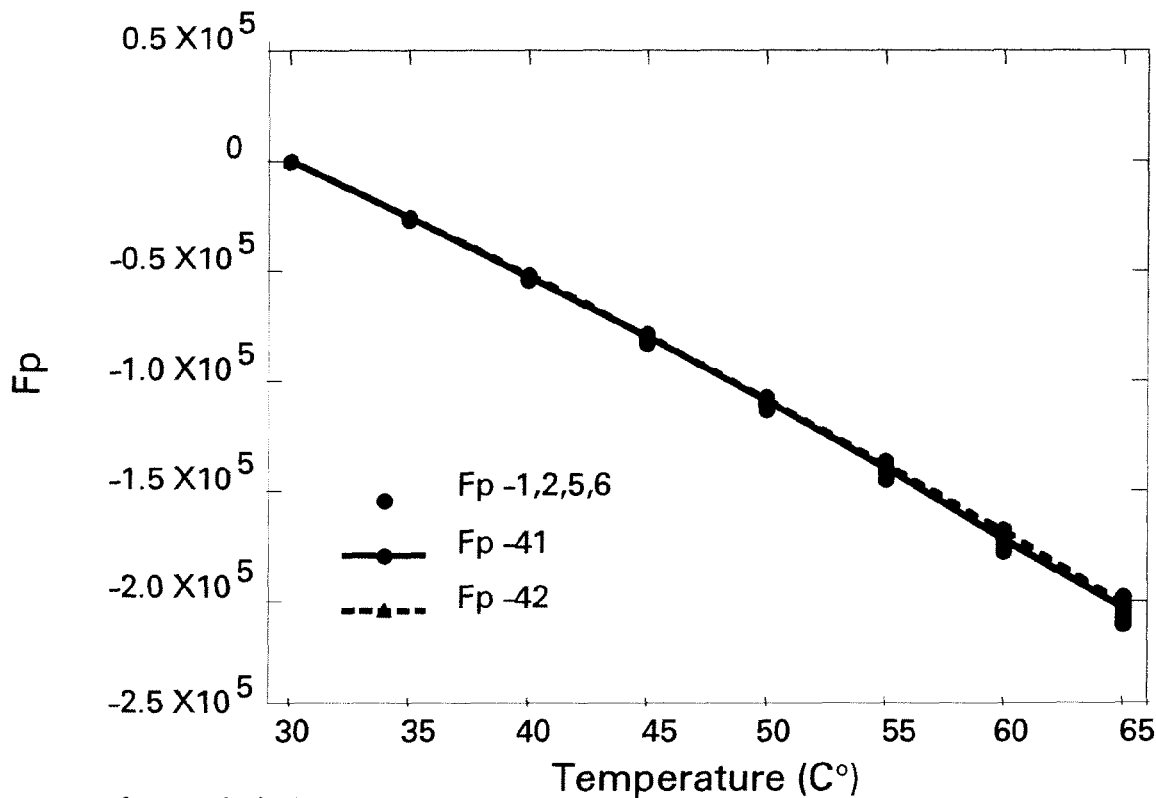

In one embodiment of the invention, RFID sensor S4 was used to demonstrate improvement in temperature measurements based on calibration. FIG. 11A illustrates the initial Fp values for RFID temperature sensor S4 (values Fp-41 and Fp-42) prior to calibration. The data demonstrates that sensor S4 has a strong offsets as compared to similarly used calibrated RFID sensors. The S4 offset is due to intentional sensor misalignment. However, when initial values Fp-41 and Fp-42 are used to calibrate the RFID sensor S4, the response of the RFID sensor S4 matched the responses of the other sensors as shown in FIG. 11B.

Example 2

Measurement of Multiple Parameters Using a Single RFID Sensor

A single RFID sensor may be used to independently determine more than one parameter. A Texas Instruments RFID tag was adapted for sensing of temperature and solution conductivity by laminating the RFID tag to a polymer film. Measurements of the complex impedance of the resulting RFID sensor were performed with a network analyzer (Model E5062A, Agilent Technologies, Inc. Santa Clara, Calif.) under computer control using LabVIEW. The network analyzer was used to scan the frequencies over the range of interest and to collect the complex impedance response from the RFID sensors. Adding NaCl salt into a vessel to which the RFID sensor was attached produced solution conductivity changes. Positioning the entire vessel and the RFID sensor into an environmental chamber where the temperature was incrementally increased from 5 to 60° C. changed the temperature.

Figure 12A:
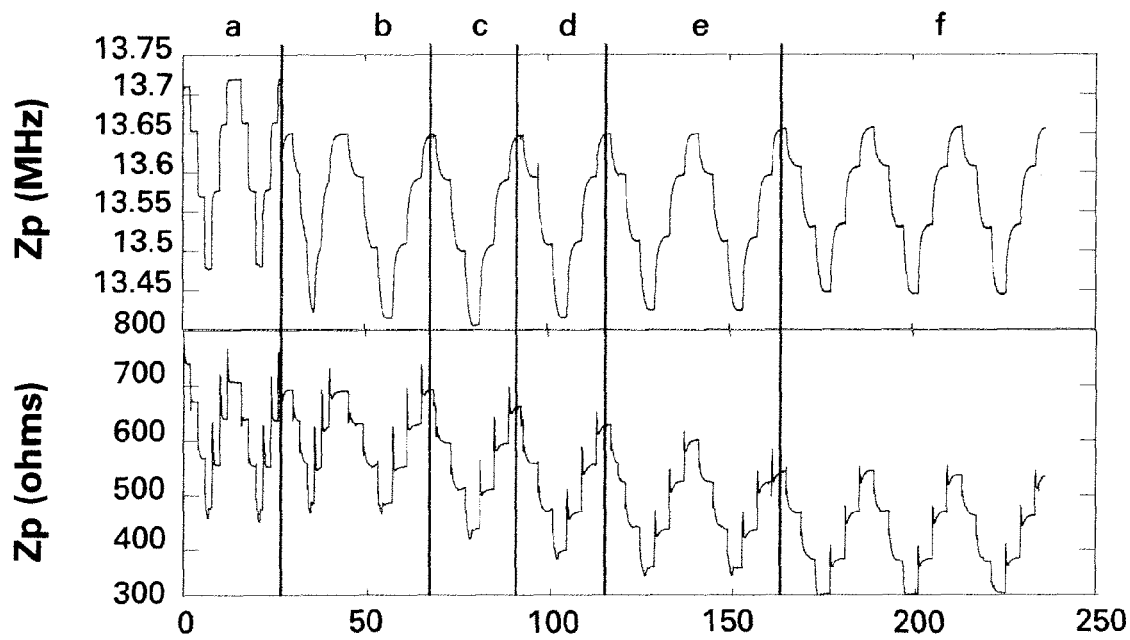
FIG. 12A shows variations in the measured responses (Fp and Zp) of an embodiment of an RFID sensor upon changes in solution conductivity and temperature.
Figure 12B:
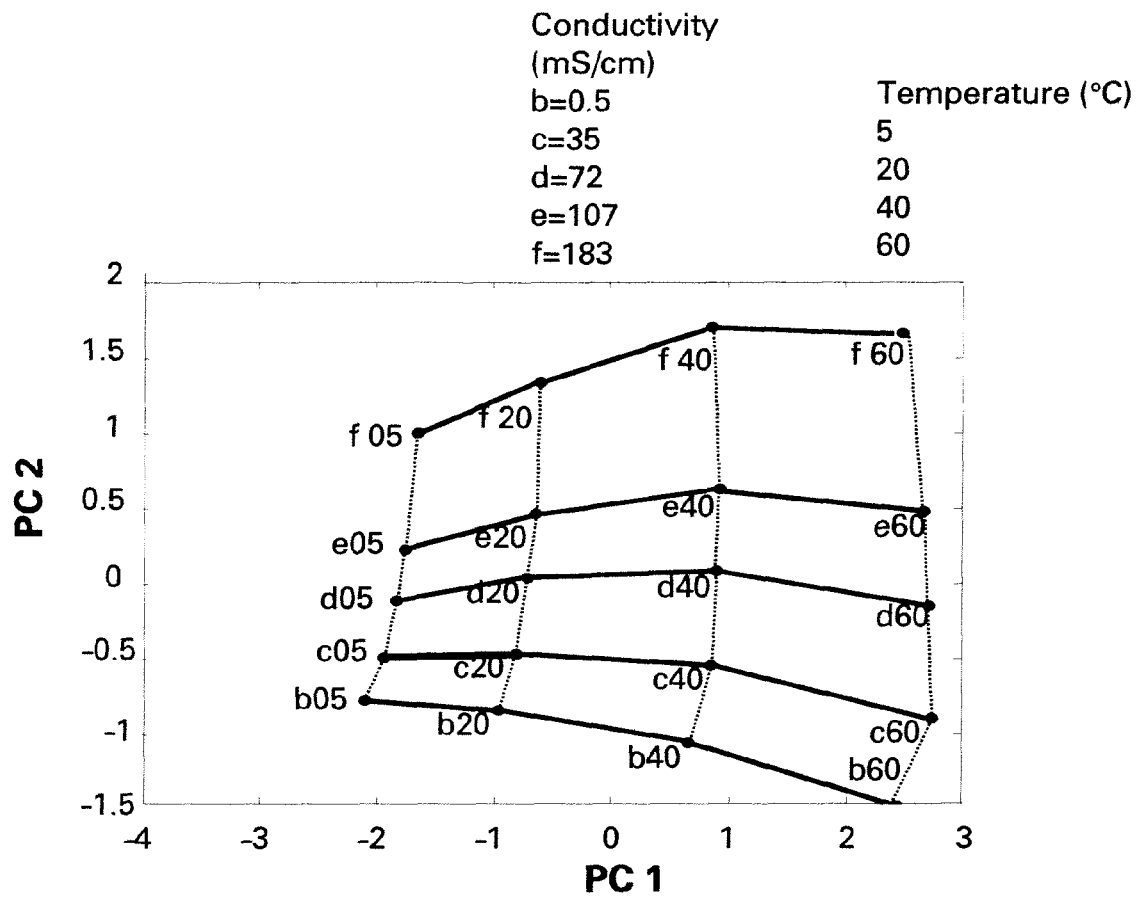
FIG. 12B shows a principal components analysis plot of the first two principal components that are related the simultaneous changes in temperature and conductivity of the solution to the multivariate response of the RFID sensor.

FIG. 12A shows variations in the measured responses (Fp and Zp) of an embodiment of an RFID sensor upon changes in solution conductivity and temperature. Initially, the sensor was kept in an empty container (region a in FIG. 12A) while the temperature was cycled between 5 and 60° C. Next deionized water was added (region b) and the temperature was cycled again between 5 and 60° C. Serial additions of NaCl over the experimental time of ~230 h (regions c, d, e, and f) produced solution conductivities of up to 183 mS/cm. All four measured parameters of complex impedance (Fp, Zp, F1, F2) were further analyzed using principal components analysis (PCA). FIG. 12B shows a principal components analysis plot of the first two principal components that related the simultaneous changes in temperature and conductivity of the solution to the multivariate response of the RFID sensor. The 2-D response (FIG. 12B) was further modeled with a non-linear 2-D response function, demonstrating the capability of measuring multiple parameters with a single RFID sensor.

Example 3

Discrimination of Chemical and Physical Measured Parameters Using a Single Complementary RFID Sensor The operation of a complementary sensor that exhibits a simultaneous resistance and capacitance change can be used to discriminate between different parameters of interest. These parameters of interest affect the sensor response in diverse ways, such that it is possible to selectively measure one or more parameters A combination humidity and temperature RFID sensor was fabricated by attaching a complementary sensor to an RFID tag. A humidity sensor (Vaisala Inc.) was attached to a Texas Instruments RFID tag across its antenna. The humidity sensor from Vaisala Inc. is a capacitor structure filled with a humidity sensitive polymer. The dielectric property of the humidity sensitive polymer changes as a function of humidity. However, these changes are also temperature sensitive. Thus, if a single response is measured from the RFID sensor, temperature and humidity effects on the signal response cannot be distinguished. Measurements of several parameters from the RFID sensor; Fp, Zp, F1, and F2 overcome this limitation.

Measurements of the complex impedance of the resulting RFID sensor were performed with a network analyzer (Model E5062A, Agilent Technologies, Inc. Santa Clara, Calif.) under computer control using LabVIEW. The network analyzer was used to scan the frequencies over the range of interest and to collect the complex impedance response from the RFID sensor. Humidity changes were produced manually by application of pulsed humid air (about 80% RH) across the sensor. Temperature changes were produced by application of a heat pulse from an incandescent lamp to about 35° C. from a room temperature (~25° C.) background response.

FIG. 13 compares the measured responses of an embodiment of an RFID sensor resulting from humidity changes, with and without an attached complementary capacitance sensor. Region A, from 0 to 500 seconds, shows measurements taken with an attached complementary sensor. Region B, from 500 to 2200 seconds, shows measurements taken without an attached complementary sensor. Changes in humidity are reflected in three large, sharp changes in the response signal. In comparison, temperature change is reflected by two smaller and broader changes in the response signal. The data shows a significantly larger signal when a complementary capacitance sensor was attached to the RFID sensor.

FIG. 14 illustrates the ability of an embodiment of an RFID sensor with a complementary sensor to discriminate between temperature and humidity effects using Fp, F1, F2, and Zp responses. As shown, the temperature effect is directionally opposite to the humidity effect when Fp, F1, and F2 responses are compared and a directionally similar effect in measuring Zp. The effect is distinctively different compared to an RFID sensor, without the attached complementary sensor. As shown in FIG. 15, when the RFID sensor without the attached complementary sensor is exposed to the same two environmental changes, the direction of the humidity and temperature effects is the same. The data demonstrates that a properly selected complementary sensor, when coupled to a data collection (F1, F2, Fp, Zp) and analysis, discriminates between environmental changes based on measured response selection.

Example 4

Discrimination of Gas Mixtures Using Complementary RFID Sensor

The operation of a complementary sensor is capable of exhibiting a diverse response upon exposure to different environmental parameters (different vapors). A vapor RFID sensor was fabricated by attaching a vapor sensitive capacitor sensor to an RFID tag. A capacitive sensor (Farnell SMTRH05) was attached to a Texas Instruments RFID tag across its antenna. The sensor capacitor was coated with polyurethane polymer. Measurements of the complex impedance of the resulting RFID sensor were performed with a network analyzer (Model E5062A, Agilent Technologies, Inc. Santa Clara, Calif.) under computer control using LabVIEW. The network analyzer was used to scan the frequencies over the range of interest and to collect the complex impedance response from the RFID sensors. Vapor changes (water vapor and toluene vapor) were produced using a computer-controlled test chamber.

Figure 17B:
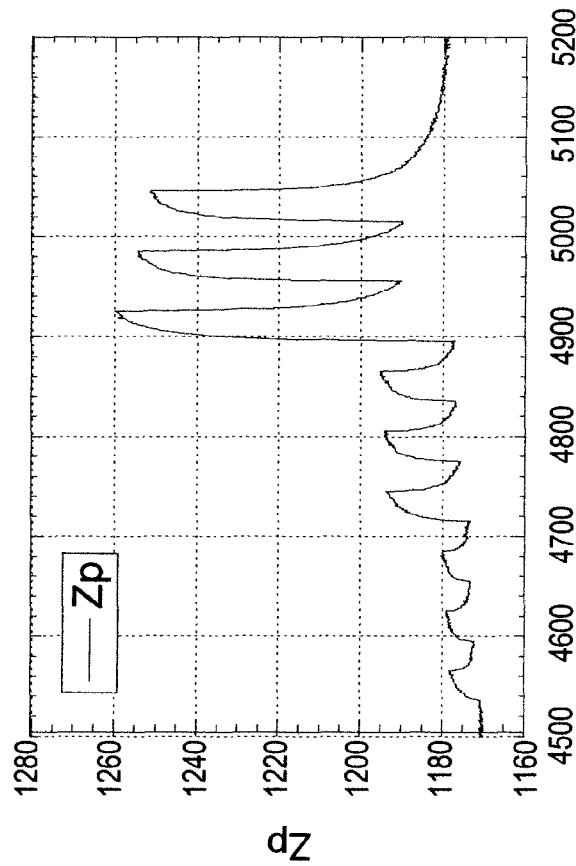
Figure 17A:
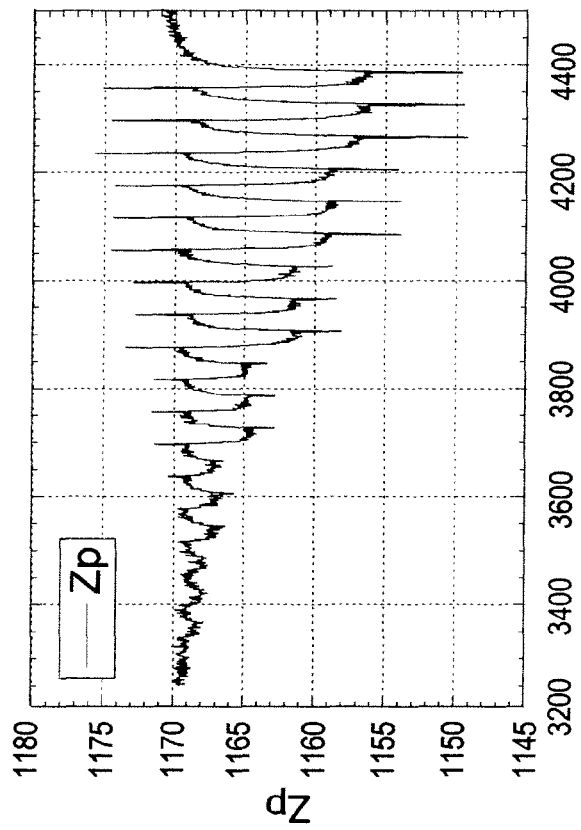

FIG. 16 shows the measured complex response of an embodiment of an RFID sensor resulting from exposure to water and toluene vapors and their mixtures. FIG. 16 illustrates 6 regions, A-F. Region A illustrates sensor response to water vapor at six increasing concentrations at three replicate responses per vapor concentration. Region B illustrates sensor response to toluene vapor at three increasing concentrations at three replicate responses per vapor concentration. Region C illustrates sensor response to water vapor at one concentration at three replicate responses at this vapor concentration. Region D illustrates sensor response to toluene vapor at one concentration at three replicate responses at this vapor concentration. Region E illustrates sensor response to a mixture of water and toluene vapors at one concentration of water and toluene vapors at three replicate responses. Region F is a repeat of sensor response to vapors concentrations and their mixtures shown in regions A-E. Regions of response to different increasing concentrations of water vapor and toluene vapor at three replicates per concentration are presented in FIG. 17. FIG. 17A shows the response to different concentrations of water vapor and FIG. 17B shows the response to different concentrations of toluene vapor.

The data illustrates that the sensor responded to these two vapors with opposite directions of the response. Calibration plots of the response of the RFID sensor are shown in FIG. 18 while FIG. 19 shows the response to individual components and mixtures of water and toluene vapor. In FIG. 19 region A corresponds to water vapor, region B corresponds to toluene vapor, and region C corresponds to a mixture of water and toluene vapors.

Results of Principal components analysis (PCA) of data from FIG. 16 are illustrated in FIG. 20. These results demonstrate that the RFID sensor was able to resolve a mixture of toluene and water vapors. These vapors affect the sensor response differently and therefore it is possible to selectively determine the nature of the vapor and vapors mixture.

Example 5

Discrimination of Individual Vapors Using Complementary RFID Sensor

A vapor sensor RFID sensor was fabricated using a 10×10 mm antenna with 100 micron spacing between coils and a 100 micron coil width, a Texas Instruments memory chip, a Seacoast Science vapor sensor, and a tuning capacitor. The tuning capacitor was configured to match the resonance response of the sensor and to allow for writing and reading of the memory chip of the sensor using a 13.56 MHz frequency band. The Seacoast Science vapor sensor is a capacitance sensor coated with a vapor-responsive gold nanoparticle-polymer composite film. Measurements of the complex impedance of the resulting RFID sensor were performed with a network analyzer (Model E5062A, Agilent Technologies, Inc. Santa Clara, Calif.) under computer control using LabVIEW. The network analyzer was used to scan frequencies over the range of interest and to collect the complex impedance response from the RFID sensors. Vapor changes (toluene vapor and acetonitrile vapor) were produced using computer control with two replicates per concentration.

FIG. 21 shows a response pattern of an embodiment of an RFID sensor having an attached capacitance vapor sensor. The peak frequency, Fp, shifts in opposite directions upon exposure to toluene and acetonitrile vapors (FIG. 21A). Similar response patterns are observed in F1 and Zp responses (FIG. 21B, 21D). However, the F2 response is different as shown in FIG. 21C. Thus, a complementary sensor can be designed to provide a diverse response to different species when a single sensor is attached to an RFID tag.

Example 6

Operation of RFID Complementary Sensor

The operation of an embodiment of a complementary sensor was performed using an interdigitated electrode array made with 1-micrometer thick gold electrodes that were 50 micrometers wide and 50 micrometers apart and formed on a silicon substrate. The electrodes were coated with a dispersion of carbon nanotubes in a polymer film. The interdigitated electrode array coated with the carbon nanotubes containing sensing film acts as a resistive complementary vapor sensor. The vapor RFID sensor was fabricated by attaching the resistive complementary sensor to a Texas Instruments RFID tag across its memory chip. Measurements of the complex impedance of the resulting RFID sensor were performed with a network analyzer (Model E5062A, Agilent Technologies, Inc. Santa Clara, Calif.) under computer control using LabVIEW. The network analyzer was used to scan frequencies over the range of interest and to collect the complex impedance response from the RFID sensor. Vapor changes were produced under computer control by bubbling dichloromethane solvent and diluting the resulting vapor with a carrier gas with a constant total flow. As a result, six different concentrations of dichloromethane vapor were generated: 0.02, 0.04, 0.7, 0.1, 0.14, and 0.2 $P/P_o$, where $P_o$ is the saturated vapor pressure. The RFID sensor was exposed to each vapor concentration with two replicates and the response is shown in FIG. 22. The data illustrates a predictive linear response based on changes in Zp.

Example 7

RFID Dosimeter for Food and Beverage Quality

An embodiment of an RFID sensor may be used for non-invasive determination of freshness of a milk beverage. Non-invasive determinations with RFID sensors were done directly through the walls of original milk cartons. Two different types of milk were used for evaluation, fat-free milk and whole milk. To determine a milk spoilage rate, RFID sensors were attached with an adhesive film to the sidewall of the milk cartons. Texas Instruments 13.56 MHz RFID tags were used for sensing changes in the dielectric properties of the two types of milk during storage. Experiments were done at room temperature. A third RFID sensor was attached to a carton filled with water and its signal change was used as a control. Sensors monitored the change in solution dielectric constant as a function of experimental storage time, at room temperature, by taking an advantage of the electromagnetic field penetration depth out of plane of the sensors and performing analysis directly through the original thin wall of the milk cartons.

Measurements of the complex impedance of three RFID sensors were performed with a network analyzer (Model E5062A, Agilent Technologies, Inc. Santa Clara, Calif.) under computer control using LabVIEW. The network analyzer was used to scan the frequencies over the range of interest and to collect the complex impedance response from the RFID sensors. FIG. 23 illustrates results of real time non-invasive monitoring of the condition of the two types of milk and the control at room temperature. The data illustrates a stable response of a control RFID sensor that monitored different rates of spoilage of whole and fat free milk and no signal change for the control RFID sensor.

The example demonstrates that a single point calibration of an RFID sensor may be determinative of dynamic processes such as food spoilage rate. In this manner a sensor may be attached to a food container and its complex impedance parameter, or its entire spectrum, at time of manufacturing or storage may be stored on the memory chip of the RFID tag for reference.

In larger scale monitoring of dynamic or steady state processes, redundant RFID sensors may be used. Redundancy improves calibration quality by reducing deviations between sensors based on sensor failure. In this manner calibration of an installed RFID sensor, is performed by using at least one control RFID sensor. With this calibration approach, the reading of the installed RFID sensor is compared to the reading of a control RFID sensor. In FIG. 23 the non-invasive monitoring of beverage containers using an embodiment of a disposable RFID sensor is shown where the control sensor does not exhibit signal change.

Example 8

RFID Dosimeter for Exposure to Toxic Industrial Chemicals

Monitoring of toxic industrial chemicals becomes critical for a variety of applications such as industrial safety and monitoring. For detection of toxic industrial chemicals such as ammonia gas, a Texas Instruments 13.56 MHz RFID tag was coated with a polyaniline polymeric film and positioned into a flow cell. Ammonia gas was introduced into the flow cell at different concentrations (4, 8, 14, 20, 28, and 40 ppm). FIG. 24 shows the measured response of an embodiment of an RFID sensor dosimeter for ammonia gas; (A) is an example of a stable signal upon exposure to ammonia gas at different concentrations, and (B) is a calibration curve for the RFID ammonia dosimeter. The width of the vertical bars (top of the graph labeled 4, 8, 14, 20, 28, and 40) is indicative of time of exposures to the ammonia gas. The RFID sensor dosimeter accumulates the individual responses to ammonia, upon an exposure to a certain ammonia concentration. The response remains effectively unchanged over a period of time making it possible to take a reading of the RFID sensor dosimeter at a later time, such as at the end of a work shift, without loss of reading accuracy.

In one embodiment, fabricating multiple RFID sensor dosimeters under the same conditions and obtaining a response to the analyte or interference of interest at different concentrations from a selected subset of the RFID sensors may be used to calibrate RFID sensor dosimeters. The response curve that is obtained is used with the remaining fabricated RFID sensor dosimeters to predict analyte or interference concentrations from their responses.

In an alternative embodiment, multiple RFID sensor dosimeters, fabricated under the same conditions may be exposed to an analyte or interference of interest and their response recorded. After construction of response curves, the RFID sensor dosimeters are reset to their original responses in the absence of an analyte.

Example 9

Improvement of RFID Response by Using Full Complex Impedance Spectrum Analysis

RFID sensor response may be improved by the analysis of the entire complex impedance spectra rather than limiting the analysis to only a single parameter or several parameters from the spectra. To validate this method, a gas RFID sensor was exposed to toluene vapor, and the RFID sensor response recorded. The signal-to-noise ratio between the amount of signal change and the noise in sensor response was evaluated.

Figure 25A:
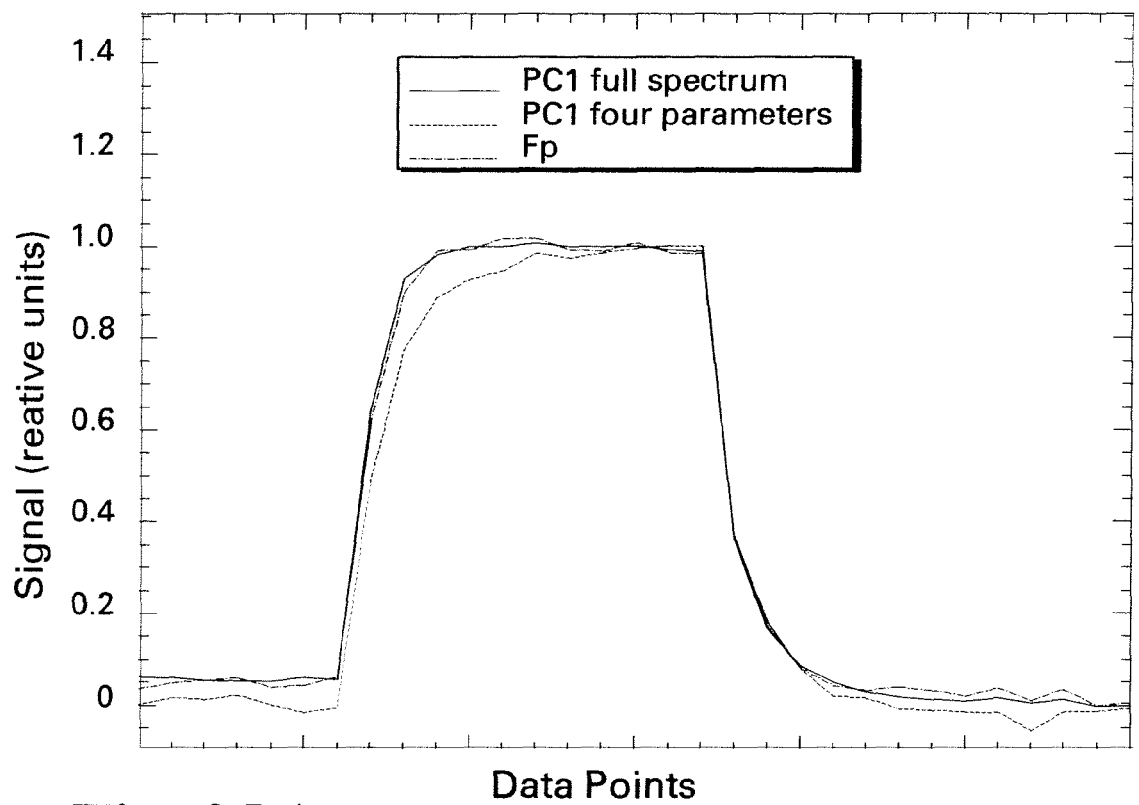
Figure 25B:
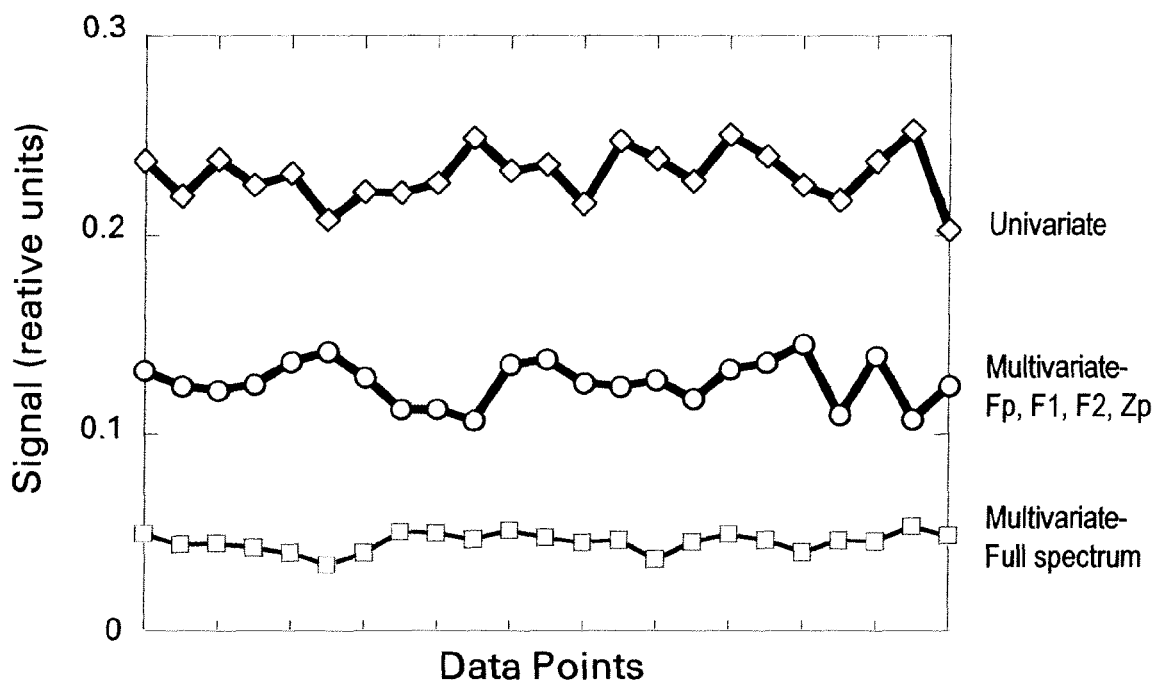

FIG. 25 shows improvement in calibrating an embodiment of an RFID sensor using univariate and multivariate calibration analysis. FIG. 25A shows three RFID sensor responses. Responses were obtained from monitoring a single parameter (Fp), monitoring a linear combination of four parameters (Fp, Zp, F1, F2) that was reduced down to a principal component, and monitoring the entire spectrum that was also reduced down to a principal component. The three RFID sensor responses were normalized so to have the same response magnitude. By comparison, FIG. 25B shows the amount of noise produced using the respective signal analysis methods. For clarity, three traces shown in FIG. 25B were offset vertically. Taking the signal intensity of the sensor response and dividing it by the amount of noise in the response calculated the signal-to-noise for each of three responses. Thus, the signal-to-noise for signal analyzed using only a univariate parameter (Fp) was 65, the signal-to-noise for signal analyzed using the multivariate response of four parameters (Fp, F1, F2, Zp) was 85, and the signal-to-noise for signal analyzed using multivariate response of the full spectrum was 200. This method of improvement of response of RFID sensor is useful for detection of small or trace analyte concentrations.

The invention claimed is:

1. A method for calibration of an RFID sensor used in manufacturing and monitoring systems comprising:
   measuring complex impedance of an RFID sensor antenna;
   relating the measurement of impedance of the RFID sensor antenna to one or more parameters;
   computing one or more analytical fit coefficients;
   storing the one or more analytical fit coefficients on a memory chip of the RFID sensor; and
   wherein measuring complex impedance comprises measuring at least one of frequency of magnitude of the real part of the complex impedance, resonance peak position of the real part of the complex impedance, resonant frequency of the imaginary part of the complex impedance, antiresonant frequency of the imaginary part of the complex impedance, zero-reactance frequency, quality factor of resonance, peak width, and peak symmetry of the complex impedance response of the antenna.

2. The method of claim 1 wherein measuring complex impedance comprises measuring phase angle and magnitude of the impedance.

3. The method of claim 1 wherein the one or more parameters are measurable variables within a manufacturing or monitoring system.

4. The method of claim 3 wherein the measurable variables comprises at least one of physical, chemical and biological properties.

5. The method of claim 4 wherein physical, chemical and biological properties comprises temperature, pressure, material concentration, conductivity, dielectric property, dose of ionizing radiation, and light intensity.

6. The method of claim 1 wherein the relating step comprises identifying a change in the measurement of complex impedance which correlates to a change in the one or more parameters.

7. The method of claim 6 wherein the change in one or more parameters relates to dimension, quantity or capacity of the one or more parameters.

8. The method of claim 6 wherein the relating step further comprises:
   identifying a change in the measurement of complex impedance which correlates to a change in one or more interference factors; and
   identifying a response relationship between the measurement of complex impedance and changes in the one or more parameters which occur in the presence of the one or more interference factors.

9. The method of claim 8 wherein the interference factors hinders, obstructs or impedes the relating the measurement of complex impedance of the RFID sensor antenna to the one or more parameters.

10. The method of claim 1 wherein the computing step comprises a univariate or a multivariate analysis.

11. The method of claim 1 wherein where the memory chip operates over at least one of the assigned radio frequency regions in the range from about 100 kHz to about 10 GHz.

12. The method of operating an RFID sensor calibrated according to claim 1 further comprising:
   measuring complex impedance of an RFID sensor during exposure to one or more parameters;
   converting the complex impedance into measurement values of the one or more parameters using the stored one or more analytical fit coefficients; and
   optionally sending the measurement values of the one or more parameters to a display device or a control device.

13. The method of claim 12 further comprising:
   obtaining measurement values of the one or more parameters using a reference measurement system;
   comparing the measurement values of the one or more parameters using the reference measurement system to the measurement values from converting the complex impedance using the stored one or more analytical fit coefficients;
   adjusting the analytical fit coefficients based on the compared measurement values; and
   storing the adjusted analytical fit coefficients on the memory chip of the RFID sensor.

14. The method of claim 13 wherein the reference measurement system comprises measuring one or more parameters using a known standard.

15. The method of claim 14 wherein the known standard comprises at least one of a control sample, a manufactured calibrator, or a calibration-set.

16. The method of claim 1 wherein the measuring complex impedance of an RFID sensor occurs during a manufacturing or a monitoring process.

17. The method of claim 1 further comprising storing digital identification on the memory chip of the RFID sensor and optionally sending the stored data to a display device or a control device.

18. The method of claim 17 wherein the digital identification comprises at least one of information regarding part identification, assembly, use, correction coefficients, calibration, production history, shelf life, and expiration date for a component associated with the RFID sensor.

19. The method of claim 1 wherein the measurement of complex impedance of an RFID sensor antenna further comprising the measurement of complex impedance of a plurality of RFID sensor antennas.

20. The method of claim 1 wherein the RFID sensor further comprises a complementary sensor.

21. The method of operating an RFID sensor calibrated according to claim 1 further comprising:
   measuring complex impedance of an RFID sensor during exposure to one or more parameters;
   converting the complex impedance into measurement values of the one or more parameters using the stored one or more analytical fit coefficients;
   storing measurement values in memory of the memory chip of the RFID sensor by writing the measurement values using a reader/writer device; and
   optionally sending the measurement values of the one or more parameters to a display device or a control device.

22. A manufacturing or monitoring system comprising an RFID sensor wherein the RFID sensor comprises:
   a memory chip;
   an antenna;
   a complementary sensor; and
   wherein the complementary sensor is configured to provide a measured response to a change in a parameter and the measured response is selected from the group consisting of a change in the resistance of the complementary sensor, a change in capacitance of the complementary sensor, a change in inductance of the complementary sensor and combinations thereof.

23. The RFID sensor of claim 22 wherein the change in a parameter is chemical, physical or biological property.

24. The RFID sensor of claim 22 wherein the complementary sensor is connected to the antenna, the memory chip, or to both the antenna and the memory chip of the RFID sensor.

25. The RFID sensor of claim 22 further comprising digital identification stored on the memory chip of the RFID sensor.

26. The RFID sensor of claim 25 wherein the digital identification comprises at least one of information regarding part identification, assembly, use, correction coefficient, calibration, production history, shelf life, and expiration date for the component associated with the RFID sensor.

27. The RFID sensor of claim 22 wherein the RFID sensor is incorporated into a manufacturing device or a monitoring device.

28. The RFID sensor of claim 27 wherein the manufacturing device or the monitoring device comprises a plurality of RFID sensors.

29. The RFID sensor of claim 22 wherein the RFID sensor is part of a network device such as a computer laptop, cell phone, or personal digital assistant (PDA) and wherein the network device has an RFID reader to read at least one RFID sensor.

* * * * *